US011214795B2

(12) United States Patent
Gopinath et al.

(10) Patent No.: US 11,214,795 B2
(45) Date of Patent: Jan. 4, 2022

(54) BISTABLE POLYNUCLEOTIDE DEVICES FOR THE SENSING AND QUANTIFICATION OF MOLECULAR EVENTS

(71) Applicant: California Institute of Technology, Pasadena, CA (US)

(72) Inventors: Ashwin Gopinath, Pasadena, CA (US); Paul W. K. Rothemund, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 363 days.

(21) Appl. No.: 16/350,115

(22) Filed: Sep. 25, 2018

(65) Prior Publication Data
US 2019/0323002 A1  Oct. 24, 2019

Related U.S. Application Data

(60) Provisional application No. 62/562,892, filed on Sep. 25, 2017.

(51) Int. Cl.
  *C12N 15/115*  (2010.01)
  *C12N 15/10*  (2006.01)
  (Continued)

(52) U.S. Cl.
  CPC ..... *C12N 15/1065* (2013.01); *G01N 33/5308* (2013.01); *G01N 33/573* (2013.01);
  (Continued)

(58) Field of Classification Search
  None
  See application file for complete search history.

(56) References Cited

U.S. PATENT DOCUMENTS 5,622,821 A * 4/1997 Selvin ............... G01N 33/533
                                                          435/6.11
8,703,734 B2   4/2014 Lyakhov et al.
(Continued)

FOREIGN PATENT DOCUMENTS

WO   WO2016/089588 A1   6/2016

OTHER PUBLICATIONS

Xu, A. et al., DNA origami: The bridge from bottom to top, MRS Bulletin, Dec. 8, 2017, vol. 42, Issue. 12, pp. 943-950.
(Continued)

*Primary Examiner* — Robert T. Crow
(74) *Attorney, Agent, or Firm* — Lewis Roca Rothgerber Christie LLP

(57) ABSTRACT

Bistable devices are constructed using a polynucleotide platform for the sensing of molecular events such as binding or conformational changes of target molecules. Uses include measurement of target concentration, measuring the effect of environmental condition (such as heat, light, or pH) on the target, or screening a library for molecules that bind the target or modulate its biological function. Devices comprise three regions: a top lid, bottom lid, and flexible linker or hinge between them. A device has an open configuration in which the top and bottom lid are separated, and a closed configuration they are bound close together. Binding domains or variations of the target molecule are fixed to a device so that when the molecular event occurs, the device switches from open to closed, or vice versa, which generates a signal. Devices carry DNA tags to enable separation of open and closed devices, as well as barcoding for multiplexed detection.

29 Claims, 23 Drawing Sheets
(23 of 23 Drawing Sheet(s) Filed in Color)

(51) Int. Cl.
*G01N 33/53* (2006.01)
*G01N 33/573* (2006.01)

(52) U.S. Cl.
CPC . *C12Q 2525/197* (2013.01); *C12Q 2525/205* (2013.01); *C12Q 2525/30* (2013.01); *G01N 2333/705* (2013.01); *G01N 2333/912* (2013.01)

(56) References Cited

U.S. PATENT DOCUMENTS

| | | | |
|---|---|---|---|
| 9,222,093 B2 | 12/2015 | Huang et al. | |
| 9,322,024 B2 | 4/2016 | Gu et al. | |
| 2006/0121470 A1* | 6/2006 | Pedersen | C07H 21/00 435/6.12 |
| 2006/0127940 A1 | 6/2006 | Bao et al. | |
| 2007/0117109 A1* | 5/2007 | Rothemund | C12N 15/10 435/6.12 |
| 2007/0154899 A1* | 7/2007 | Coull | C12Q 2523/101 435/6.12 |
| 2012/0287244 A1 | 11/2012 | Bennett et al. | |
| 2013/0261019 A1* | 10/2013 | Lin | C12Q 1/6825 506/9 |
| 2014/0179540 A1 | 6/2014 | Downtown et al. | |
| 2020/0025752 A1 | 1/2020 | Gopinath et al. | |

OTHER PUBLICATIONS

International Search Report and Written Opinion issued in corresponding PCT Application No. PCT/US2018/000377, dated Dec. 26, 2018, 28 pages.
Afsahi et al, "Towards Novel Graphene-Enabled Diagnostic Assays with Improved Signal-to-Noise Ratio" MRS Advances 60 (2017) 3733-3739.
Allen et al, "Carbon Nanotube Field-Effect-Transistor-Based Biosensors" Advanced Materials 19 (2007) 1439-1451.
Barbulovic-Nad et al "Bio-microarray fabrication techniques—a review." Critical Reviews in Biotechnology. 26 (2006):237-59.
Bayburt et al, "Membrane Protein Assembly into Nanodiscs" FEBS Letters 584 (2010):1721-1727.
Chen et al, "Silicon nanowire field-effect transistor-based biosensors for biomedical diagnosis and cellular recording investigation" Nanotoday 6 (2011) 131-154.
Chworos, Arkadiusz, et al., "Building programmable jigsaw puzzles with RNA." Science 306 (2004):2068-72.
Dulkeith et al, "Gold Nanoparticles Quench Fluorescence by Phase Induced Radiative Rate Suppression" Nano Letters 5 (2005):585-589.
Geary, Cody, et al., "A single-stranded architecture for cotranscriptional folding of RNA nanostructures", Science 345 (2014) 799-804.
Gerdon et al, "Controlled Delivery of DNA Origami on Patterned Surfaces", Small 5 (2009): 1942-1946.
Gietl et al "DNA origami as biocompatible surface to match single-molecule and ensemble experiments" Nucleic Acids Res. 40 (2012): e110.
Gopinath et al, "Optimized Assembly and Covalent Coupling of Single-Molecule DNA Origami Nanoarrays", ACS Nano 8 (2014): 12030-12040.
Gopinath et al, "Engineering and mapping nanocavity emission via precision placement of DNA origami", Nature 535 (2016): 401-405.
Han et al, "DNA origami with complex curvatures in three-dimensional space", Science 332 (2011): 342-346.
Han, Dongran, et al., "Single-stranded DNA and RNA origami", Science 358 (2017): eaao2648.
Hung et al, "Large-area spatially ordered arrays of gold nanoparticles directed by lithographically confined DNA origami", Nature Nanotechnology 5 (2010): 121-126.
Immoos et al, "DNA-PEG-DNA triblock macromolecules for reagentless DNA detection", Journal of the American Chemical Society 126 (2004): 10814-10815.

Iric et al "DNA-Encircled Lipid Bilayers" Nanoscale (2018) DOI:10.1039/C8NR06505E).
Kasry et al, "Highly Efficient Fluorescence Quenching with Graphene" J. Phys. Chem. C 116 (2012):2858-2862.
Ke, Yonggang, et al., "Three-Dimensional Structures Self-Assembled from DNA Bricks", Science 338 (2012): 1177-1183.
Kershner et al, "Placement and orientation of individual DNA shapes on lithographically patterned surfaces", Nature Nanotechnology 4 (2009):557-561.
Kinkhabwala, et al. "Large single-molecule fluorescence enhancements produced by a bowtie nanoantenna", Nature Photonics 3 (2009):654-657.
Lai, "Chapter Eight: Folding- and Dynamics-Based Electrochemical DNA Sensors", Methods in Enzymology, 589 (2017):221-252.
Lemay et al, "Single-Molecule Electrochemistry: Present Status and Outlook" Acc. Chem. Res. 46 (2013): 369-377.
Maune et al, "Self-assembly of carbon nanotubes into two-dimensional geometries using DNA origami templates" Nature Nanotechnology (2010) 61-66.
Nakatsuka, et al, "Aptamer-field-effect transistors overcome Debye length limitations for small-molecule sensing", Science 6 (2018) eaao6750.
Oakes et al "Profiling of engineering hotspots identifies an allosteric CRISPR-Cas9 switch", Nature Biotechnology 34 (2016):646-651.
Ricci et al, "Linear, redox modified DNA probes as electrochemical DNA sensors" Chemical Communications 36(2007): 3768-3770.
Rothemund, Paul WK. "Folding DNA to create nanoscale shapes and patterns", Nature 440.7082 (2006): 297.
Sarkaleh et al, "Optical Ring Resonators: A Platform for Biological Sensing Applications" J. Med. Signals. Sens. 7 (2017):185-191.
Sarkar et al, "MoS$_2$ Field-Effect Transistor for Next-Generation Label-Free Biosensors", ACS Nano 8 (2014) 3992-4003.
Selvin et al, "Luminescence Resonance Energy Transfer" Journal of the American Chemical Society, 116(1994):6029-6030.
Sun et al "A Scalable High-Density Electrochemical Biosensor Array for Parallelized Point-of-Care Diagnostics", 2015 IEEE Biomedical Circuits and Systems Conference, IEEE Journal of Solid-State Circuits 53 (2018) 2054-2064.
Torelli, Emanuela et al, "Isothermal folding of a light-up bio-orthogonal RNA origami nanoribbon", Scientific Reports 8 (2018): 6989.
Tsukanov et al, "Detailed study of DNA hairpin dynamics using single-molecule fluorescence assisted by DNA origami", Phys. Chem. B 117 (2013):11932-11942.
Veigas et al, "Field Effect Sensors for Nucleic Acid Detection: Recent Advances and Future Perspectives" Sensors 15 (2015):10380-10398.
Wang, Pengfei, et al. "RNA-DNA hybrid origami: folding of a long RNA single strand into complex nanostructures using short DNA helper strands", Chemical Communications 49 (2013) 5462-5464.
Wei, Bryan, et al., "Complex shapes self-assembled from single-stranded DNA tiles", Nature 485 (2012):623-626.
Winfree, Erik, et al., "Design and self-assembly of two-dimensional DNA crystals", Nature 394 (1998) 539-44.
Wu et al, "Development of a "signal-on" electrochemical DNA sensor with an oligo-thymine spacer for point mutation detection", Chemical Communications, 49 (2013): 3422-3424.
Wu, et al, "Effects of DNA Probe and Target Flexibility on the Performance of a "Signal-on" Electrochemical DNA Sensor" Analytical Chemistry 86 (2014) 8888-8895.
Zhao et al, DNA-Corralled Nanodiscs for the Structural and Functional Characterization of Membrane Proteins and Viral Entry, Journal of the American Chemical Society, 140 (2018): 10639-10643.
Zhou et al. "A plasmonic nanorod that walks on DNA origami" Nature Communications 6 (2015):8102.
Zhou et al, "Tandem phosphorothioate modifications for DNA adsorption strength and polarity control on gold nanoparticles." ACS Applied Materials Interfaces 6 (2014):14795-147800.
Zhang et al, "Dynamic DNA nanotechnology using strand-displacement reactions", Nature Chemistry 3 (2011): 103-113.

\* cited by examiner open flytrap on mica surface (top view)

dsDNA linker

|—————| 100 nm

X Y   20-mer DNA of interest

★   signaling molecule, e.g. methylene blue:

*Functional Actuation*
*(Modification example using MAPK)*

*Functional Actuation (GPCR receptor + protein / lipid nanodisc)*

Functional Actuation (DNA or RNA Riboswitch exposing DNA or RNA linker)

Functional Actuation (Example RNA Riboswitch exposing MS2 binding domain for binding MCP)

Functional Actuation (Ligation)

Functional Actuation (Cleavage)

Field effect biosensing
(classical transistor)

Field effect biosensing
(low dimensional material)

Electrochemical detection

BISTABLE POLYNUCLEOTIDE DEVICES FOR THE SENSING AND QUANTIFICATION OF MOLECULAR EVENTS

CROSS-REFERENCE TO RELATED APPLICATION(S)

The present application claims priority to and the benefit of U.S. Provisional Application Ser. No. 62/562,892 filed on Sep. 25, 2017, entitled "Quantitative Origami Assisted Sandwich Immuno-sorbant (OASIS) Assay," the entire content of which is incorporated herein by reference.

STATEMENT REGARDING FEDERALLY SPONSORED RESEARCH OR DEVELOPMENT

This invention was made with government support under Grant No. CMMI1636364 awarded by the National Science Foundation and Grant No. N00014-14-1-0702 awarded by the Office of Naval Research. The government has certain rights in the invention

FIELD

The present invention relates to structures for the sensing and quantification of molecular events such as binding events, conformational changes, chemical modifications, or enzymatic modifications that may happen to a molecule of interest, for example where the quantification of such molecular events may enable the measurement of the concentration of a single analyte, or the multiplexed detection and quantification of a set of analytes, where an analyte is a type of molecule or particle in a fluid sample.

BACKGROUND

Various molecular entities exhibit selective affinity to each other, which results in the formation of a multimolecular complex, such as a receptor-ligand, antibody-antigen, or aptamer-target complex. Such selective affinity of one molecule to another is of particular interest as the binding events that result from such affinities can be used to determine the presence of an analyte in a given sample solution and, in certain settings, to also determine the concentration of analyte.

Over the last few decades, various detection methodologies have been developed based on identification of specific complex formation, including direct or indirect strategies that detect and/or amplify signals related to primary or secondary binding events, where signals could be optical (spectroscopic, colorimetric or fluorescent) or electrical (impedance, capacitance, inductance or current). Owing to the specificity, speed and sensitivity of these methods (and associated systems) they have become the cornerstone of modern analytical measurements and find utility in academic as well as industrial research. A few of the specific application area of such platforms include: environmental assessment, food safety, medical diagnosis, and detection of chemical, biological and/or radiological warfare agents.

However, existing high-sensitivity assays have technical details that make them very difficult to multiplex for multiple analytes. Further, approaches to use such assays for quantification often involve a series of dilution steps which lead to a large amount of sample. Thus there is a large need for simultaneously highly sensitive, modular, multiplexable methods to quantitatively measure the presence of analyte in small sample volumes.

More generally, the detection of molecular events such as conformational changes and enzymatic modifications can be used to create powerful assays for biological activity. For example, transmembrane protein receptors bind endogenous ligands in the course of their natural function, but artificial ligands for such receptors constitute one of the most important classes of pharmaceuticals. Activation of a transmembrane receptor by a ligand on the extracellular side is often accompanied by a conformational change, or a phosphorylation of the receptor on its cytosolic side, providing a direct indication of receptor activation, and likely biological activity. Currently, screening large libraries of molecules for potential drugs is best performed on cells. Thus there is a need for in vitro sensors of arbitrary molecular events, which can go beyond simple binding of an analyte to provide an assay for some functional molecular event, such as phosphorylation or a conformational change. Similarly screening molecules for all kinds of functional properties, such as activities that change based on heat, light, pH, or other environmental stimulus would benefit from a sensitive, modular, and multiplexable platform for arbitrary molecular events.

SUMMARY

Aspects of embodiments of the present invention relates to a general platform for detecting molecular events, such as binding events, conformational changes, chemical modifications, or enzymatic modifications which may occur to a molecule of interest. In some embodiments, the detection of a molecular event such as binding may be used to determine the concentration of molecules or particles in a fluid sample. In some embodiments, the detection of a molecular event such as a conformational change or enzymatic modification may be used to screen a library of drug candidates for activity towards a membrane receptor of medical interest.

In some embodiments of the present disclosure, a structure for detecting a selected stimulus includes a bistable molecular sensor including a polynucleotide platform forming a first shape and a second shape, the first shape connected to the second shape by a linker, the polynucleotide platform having an open state and a closed state, the open state comprising the first shape and the second shape being apart from each other by at least a first distance and the closed state comprising the first shape and the second shape being at or less than a second distance from each other, the first distance being greater than the second distance; a substrate having a surface on which one of the first shape or second shape is immobilized; and one or more functional molecules bound to the first shape and/or the second shape, the one or more functional molecules capable of actuating the bistable molecular sensor from the opened state to the closed state in the presence of a selected stimulus.

In some embodiments of the present disclosure, the structure for detecting a selected stimulus as disclosed above, wherein the first distance is dependent upon a length and flexibility of the linker.

In some embodiments of the present disclosure, the structure for detecting a selected stimulus as disclosed above, wherein the second distance is no more than lambda/10 nanometers.

In some embodiments of the present disclosure, the structure for detecting a selected stimulus as disclosed above, wherein the polynucleotide platform is selected from scaffolded deoxyribonucleic acid (DNA) origami, scaffolded ribonucleic acid (RNA) origami, scaffolded hybrid DNA: RNA origami, single-stranded DNA tiles, multi-stranded DNA tiles, single-stranded RNA origami, multi-stranded RNA tiles, or hierarchically composed DNA or RNA origami with multiple scaffolds.

In some embodiments of the present disclosure, the structure for detecting a selected stimulus as disclosed above, wherein the selected stimulus is a target molecule.

In some embodiments of the present disclosure, the structure for detecting a selected stimulus as disclosed above, wherein the one or more functional molecules include a first antibody and a second antibody, the first antibody capable of binding a first epitope on the target molecule and the second antibody capable of binding a second epitope on the target molecule, the first epitope being different from the second epitope.

In some embodiments of the present disclosure, the structure for detecting a selected stimulus as disclosed above, wherein: one or more of the first antibody are bound to the first shape inside surface, one or more of the second antibody are bound to the second shape inside surface, and the binding of the target molecule to the first antibody and the second antibody actuates the bistable molecular sensor from the opened state to the closed state.

In some embodiments of the present disclosure, the structure for detecting a selected stimulus as disclosed above, wherein the target molecule is a target single-stranded nucleic acid, the one or more functional molecules include a first probe single-stranded nucleic acid and a second probe single-stranded nucleic acid each of which are complementary to a different region of the target single-stranded nucleic acid, the first probe single-stranded nucleic acid bound to the first shape inside surface and the second probe single-stranded nucleic acid bound to the second shape inside surface, and the binding of the target single-stranded nucleic acid to the first probe single-stranded nucleic acid and the second probe single-stranded nucleic acid is capable of actuating the bistable molecular sensor from the opened state to the closed state.

In some embodiments of the present disclosure, the structure for detecting a selected stimulus as disclosed above, wherein the target molecule is a target double-stranded nucleic acid, the one or more functional molecules include a first endonuclease and guide RNA (gRNA) complex and a second endonuclease and gRNA complex each of which is capable of binding a different region of the target double-stranded nucleic acid, the first endonuclease and gRNA complex bound to the first shape inside surface and the second endonuclease and gRNA complex bound to the second shape inside surface, and the binding of the target double-stranded nucleic acid to the first endonuclease and gRNA complex and the second endonuclease and gRNA complex actuates the bistable molecular sensor from the opened state to the closed state.

In some embodiments of the present disclosure, the structure for detecting a selected stimulus as disclosed above, wherein the target molecule is a target double-stranded nucleic acid, the one or more functional molecules comprise an allosteric endonuclease and gRNA complex comprising a hidden nucleotide region and a probe nucleotide complementary to the hidden nucleotide, the allosteric endonuclease and gRNA complex bound to the first shape inside surface and the probe nucleotide bound to the second shape inside surface, and the binding of the target double-stranded nucleic acid to the allosteric endonuclease and gRNA complex presents the hidden nucleotide region for binding with the probe nucleotide thereby actuating the bistable molecular sensor from the opened state to the closed state.

In some embodiments of the present disclosure, the structure for detecting a selected stimulus as disclosed above, wherein the one or more functional molecules include a competitor for the target molecule and an antibody capable of binding the target molecule and the competitor, the competitor being bound to the first shape inside surface and the antibody being bound the second shape inside surface, wherein in the absence of the target molecule, the competitor binds to the antibody and in the presence of the target molecule, the competitor is displaced and actuates the bistable molecular sensor from the closed state to the opened state.

In some embodiments of the present disclosure, the structure for detecting a selected stimulus as disclosed above, wherein the one or more functional molecules include a first protein and a second protein, the first protein capable of being chemically or enzymatically modified by the target molecule, the second protein capable of binding the first protein when it is chemically or enzymatically modified, the first protein bound to the first shape inside surface and the second protein bound to the second shape inside surface, and the binding of the first protein to the second protein actuates the bistable molecular sensor from the opened state to the closed state.

In some embodiments of the present disclosure, the structure for detecting a selected stimulus as disclosed above, wherein the chemical or enzymatic modification of the first protein is selected from phosphorylation, acetylation, ubiquitination, prenylation, adenylylation, or glycosylation.

In some embodiments of the present disclosure, the structure for detecting a selected stimulus as disclosed above, wherein the second protein is a naturally occurring protein.

In some embodiments of the present disclosure, the structure for detecting a selected stimulus as disclosed above, wherein the second protein is an antibody capable of selectively binding the first protein when it is chemically or enzymatically modified.

In some embodiments of the present disclosure, the structure for detecting a selected stimulus as disclosed above, wherein the one or more functional molecules include a first probe nucleic acid and a first probe molecule, the first probe nucleic acid capable of being chemically or enzymatically modified and the second probe molecule capable of binding the first probe nucleic acid when the first probe nucleic acid is chemically or enzymatically modified, the first probe nucleic acid bound to the first shape inside surface and the second probe molecule bound to the second shape inside surface, and the binding of the first probe nucleic acid to the second probe molecule actuates the bistable molecular sensor from the opened state to the closed state.

In some embodiments of the present disclosure, the structure for detecting a selected stimulus as disclosed above, wherein the chemical or enzymatic modification of the first probe nucleic acid is selected from cytosine methylation, cytosine hydroxymethylation, cytosine formylation, cytosine carboxylation, adenosine methylation, alkylation, or thymine dimerization.

In some embodiments of the present disclosure, the structure for detecting a selected stimulus as disclosed above, wherein the second probe molecule is a naturally-occurring molecule.

In some embodiments of the present disclosure, the structure for detecting a selected stimulus as disclosed above, wherein the second probe molecule is an antibody capable of binding the first probe nucleic acid when it is chemically or enzymatically modified.

In some embodiments of the present disclosure, the structure for detecting a selected stimulus as disclosed above, wherein the one or more functional molecules include a first protein and a second protein, the first protein being a transmembrane receptor capable of binding at least one type of ligand and the second protein capable of binding the first protein when the first protein is bound by the at least one type of ligand, the first protein bound to the first shape inside surface and the second protein bound to the second shape inside surface, and the binding of the first protein to the second protein actuates the bistable molecular sensor from the opened state to the closed state.

In some embodiments of the present disclosure, the structure for detecting a selected stimulus as disclosed above, wherein the first protein is bound to the first shape inside surface using a binding moiety selected from: a linker molecule conjugated to the first protein and bound to directly or indirectly to the first shape inside surface and a protein-lipid nanodisc or a DNA-lipid nanodisc comprising the first protein and bound to the first shape inside surface.

In some embodiments of the present disclosure, the structure for detecting a selected stimulus as disclosed above, further comprising a third protein, wherein the first protein is a G-protein coupled receptor (GPCR), the second protein is beta-arrestin, and the third protein is a soluble or polynucleotide platform-bound G-protein receptor kinase (GRK), and wherein the beta-arrestin is capable of binding the GPCR if GRK has phosphorylated the ligand-bound GPCR, thereby actuating the bistable molecular sensor from the opened state to the closed state.

In some embodiments of the present disclosure, the structure for detecting a selected stimulus as disclosed above, wherein the target molecule is a target ligand, the one or more functional molecules include a DNA or RNA riboswitch capable of binding the target ligand and a probe molecule including a DNA sequence or an RNA sequence or a protein capable of binding the DNA or RNA riboswitch when bound to the ligand, the DNA or RNA riboswitch bound to the first shape inside surface and the probe molecule bound to the second shape inside surface, and the binding of the probe molecule to the DNA or RNA riboswitch actuates the bistable molecular sensor from the opened state to the closed state.

In some embodiments of the present disclosure, the structure for detecting a selected stimulus as disclosed above, wherein the target molecule is a chemical or enzymatic agent, the one or more functional molecules is a single molecule selected from a protein or a nucleic acid capable of being cleaved by the chemical or enzymatic agent, the single molecule attached to both the first shape inside surface and the second shape inside surface, and the cleaving of the single molecule in the presence of the target molecule actuates the bistable molecular sensor from the closed state to the opened state.

In some embodiments of the present disclosure, the structure for detecting a selected stimulus as disclosed above, wherein the one or more functional molecules include a first molecule and a second molecule, the first molecule capable of binding the second molecule upon modification of the first and/or the second molecule in the presence of a selected stimulus, the first molecule bound to the first shape inside surface and the second molecule bound to the second shape inside surface, and the binding of the first molecule to the second molecule actuates the bistable molecular sensor from the closed state to the opened state.

In some embodiments of the present disclosure, the structure for detecting a selected stimulus as disclosed above, wherein the first molecule and the second molecule are selected from a first protein and a second protein or a first nucleic acid and a second nucleic acid, the selected stimulus is selected from a chemical agent, an enzyme, temperature, light, acidity (pH), and/or ionic state, and the modification is selected from a chemical modification, enzymatic modification, or a conformational or structural change in one of the first molecule or the second molecule as a result of the presence of or a change in the temperature, the light, the pH, or the ionic conditions.

In some embodiments of the present disclosure, the structure for detecting a selected stimulus as disclosed above, wherein the non-immobilized first shape or the non-immobilized second shape further comprises a light emitter selected from an organic fluorophore, a quantum dot, a fluorescent bead, or a luminescent lanthanide compound, the substrate surface on which one of the first shape or the second shape is immobilized is capable of quenching the light emitter when it has a proximal distance to the substrate surface, the substrate surface being selected from gold or graphene, wherein the bistable molecular sensor produces more light from the opened state than the closed state.

In some embodiments of the present disclosure, the structure for detecting a selected stimulus as disclosed above, wherein the proximal distance is lamda/10 where lambda corresponds to the wavelength of light of the light emitter.

In some embodiments of the present disclosure, the structure for detecting a selected stimulus as disclosed above, further comprising a microfabricated device capable of enhancing light produced from the light emitter wherein the bistable molecular sensor is positioned within the microfabricated, the microfabricated device being selected from a photonic crystal cavity, a ring resonator, or an optical bowtie.

In some embodiments of the present disclosure, the structure for detecting a selected stimulus as disclosed above, wherein the substrate surface is transparent, the non-immobilized first shape or the non-immobilized second shape further includes a light emitter selected from a fluorescent label, a luminescent label, or a light-scattering particle, the light being emitted is of a wavelength of lambda nanometers, the linker having a length allowing for the opened state to be greater than a distance of lambda/10 nanometers, and the light produced from the bistable molecular sensor is optically detected using total internal reflection microscopy (TIRF).

In some embodiments of the present disclosure, the structure for detecting a selected stimulus as disclosed above, wherein the bistable molecular sensor in the closed state is detected optically.

In some embodiments of the present disclosure, the structure for detecting a selected stimulus as disclosed above, further including a plurality of the bistable molecular sensors wherein each of the plurality of the bistable molecular sensors are positioned at selected locations on the substrate surface by directed self-assembly.

In some embodiments of the present disclosure, the structure for detecting a selected stimulus as disclosed above, further including a plurality of the bistable molecular sensors wherein each of the plurality of the bistable molecular sensors are positioned using one or more lithographically patterned binding sites that are adhesive to the immobilized first shape or the immobilized second shape and wherein the substrate surface and the nonimmobilized shape are mutually nonadhesive.

In some embodiments of the present disclosure, the structure for detecting a selected stimulus as disclosed above, wherein the one or more lithographically patterned binding sites is a regular grid.

In some embodiments of the present disclosure, a structure for detecting a selected stimulus includes a bistable molecular sensor including: a polynucleotide platform forming a first shape and a second shape, the first shape connected to the second shape by a linker, the polynucleotide platform having an open state and a closed state, the open state including the first shape and the second shape being apart from each other by at least a first distance and the closed state comprising the first shape and the second shape being at or less than a second distance from each other, the first distance being greater than the second distance; a substrate having a surface on which one of the first shape or second shape is immobilized; and one or more functional molecules bound to the first shape and/or the second shape, the one or more functional molecules capable of actuating the bistable molecular sensor from the opened state to the closed state in the presence of a selected stimulus.

In some embodiments of the present disclosure, the structure for detecting a selected stimulus as disclosed above, wherein the first distance is dependent upon a length and flexibility of the linker.

In some embodiments of the present disclosure, the structure for detecting a selected stimulus as disclosed above, wherein the second distance is no more than 20 nanometers.

In some embodiments of the present disclosure, the structure for detecting a selected stimulus as disclosed above, wherein the polynucleotide platform is selected from scaffolded deoxyribonucleic acid (DNA) origami, scaffolded ribonucleic acid (RNA) origami, scaffolded hybrid DNA: RNA origami, single-stranded DNA tiles, multi-stranded DNA tiles, single-stranded RNA origami, multi-stranded RNA tiles, or hierarchically composed DNA or RNA origami with multiple scaffolds.

In some embodiments of the present disclosure, the structure for detecting a selected stimulus as disclosed above, wherein the selected stimulus is a target molecule.

In some embodiments of the present disclosure, the structure for detecting a selected stimulus as disclosed above, wherein the one or more functional molecules include a first antibody and a second antibody, the first antibody capable of binding a first epitope on the target molecule and the second antibody capable of binding a second epitope on the target molecule, the first epitope being different from the second epitope.

In some embodiments of the present disclosure, the structure for detecting a selected stimulus as disclosed above, wherein: one or more of the first antibody are bound to the first shape inside surface, one or more of the second antibody are bound to the second shape inside surface, and the binding of the target molecule to the first antibody and the second antibody actuates the bistable molecular sensor from the opened state to the closed state.

In some embodiments of the present disclosure, the structure for detecting a selected stimulus as disclosed above, wherein: the target molecule is a target single-stranded nucleic acid, the one or more functional molecules include a first probe single-stranded nucleic acid and a second probe single-stranded nucleic acid each of which are complementary to a different region of the target single-stranded nucleic acid, the first probe single-stranded nucleic acid bound to the first shape inside surface and the second probe single-stranded nucleic acid bound to the second shape inside surface, and the binding of the target single-stranded nucleic acid to the first probe single-stranded nucleic acid and the second probe single-stranded nucleic acid is capable of actuating the bistable molecular sensor from the opened state to the closed state.

In some embodiments of the present disclosure, the structure for detecting a selected stimulus as disclosed above, wherein: the target molecule is a target double-stranded nucleic acid, the one or more functional molecules include a first endonuclease and guide RNA (gRNA) complex and a second endonuclease and gRNA complex each of which is capable of binding a different region of the target double-stranded nucleic acid, the first endonuclease and gRNA complex bound to the first shape inside surface and the second endonuclease and gRNA complex bound to the second shape inside surface, and the binding of the target double-stranded nucleic acid to the first endonuclease and gRNA complex and the second endonuclease and gRNA complex actuates the bistable molecular sensor from the opened state to the closed state.

In some embodiments of the present disclosure, the structure for detecting a selected stimulus as disclosed above, wherein: the target molecule is a target double-stranded nucleic acid, the one or more functional molecules include an allosteric endonuclease and gRNA complex comprising a hidden nucleotide region and a probe nucleotide complementary to the hidden nucleotide, the allosteric endonuclease and gRNA complex bound to the first shape inside surface and the probe nucleotide bound to the second shape inside surface, and the binding of the target double-stranded nucleic acid to the allosteric endonuclease and gRNA complex presents the hidden nucleotide region for binding with the probe nucleotide thereby actuating the bistable molecular sensor from the opened state to the closed state.

In some embodiments of the present disclosure, the structure for detecting a selected stimulus as disclosed above, wherein the one or more functional molecules include a competitor for the target molecule and an antibody capable of binding the target molecule and the competitor, the competitor being bound to the first shape inside surface and the antibody being bound the second shape inside surface, wherein in the absence of the target molecule, the competitor binds to the antibody and in the presence of the target molecule, the competitor is displaced and actuates the bistable molecular sensor from the closed state to the opened state.

In some embodiments of the present disclosure, the structure for detecting a selected stimulus as disclosed above, wherein the one or more functional molecules include a first protein and a second protein, the first protein capable of being chemically or enzymatically modified by the target molecule, the second protein capable of binding the first protein when it is chemically or enzymatically modified, the first protein bound to the first shape inside surface and the second protein bound to the second shape inside surface, and the binding of the first protein to the second protein actuates the bistable molecular sensor from the opened state to the closed state.

In some embodiments of the present disclosure, the structure for detecting a selected stimulus as disclosed above, wherein the chemical or enzymatic modification of the first protein is selected from phosphorylation, acetylation, ubiquitination, prenylation, adenylylation, or glycosylation.

In some embodiments of the present disclosure, the structure for detecting a selected stimulus as disclosed above, wherein the second protein is a naturally occurring protein.

In some embodiments of the present disclosure, the structure for detecting a selected stimulus as disclosed above, wherein the second protein is an antibody capable of selectively binding the first protein when it is chemically or enzymatically modified.

In some embodiments of the present disclosure, the structure for detecting a selected stimulus as disclosed above, wherein the one or more functional molecules include a first probe nucleic acid and a first probe molecule, the first probe nucleic acid capable of being chemically or enzymatically modified and the second probe molecule capable of binding the first probe nucleic acid when the first probe nucleic acid is chemically or enzymatically modified, the first probe nucleic acid bound to the first shape inside surface and the second probe molecule bound to the second shape inside surface, and the binding of the first probe nucleic acid to the second probe molecule actuates the bistable molecular sensor from the opened state to the closed state.

In some embodiments of the present disclosure, the structure for detecting a selected stimulus as disclosed above, wherein the chemical or enzymatic modification of the first probe nucleic acid is selected from cytosine methylation, cytosine hydroxymethylation, cytosine formylation, cytosine carboxylation, adenosine methylation, alkylation, or thymine dimerization.

In some embodiments of the present disclosure, the structure for detecting a selected stimulus as disclosed above, wherein the second probe molecule is a naturally-occurring molecule.

In some embodiments of the present disclosure, the structure for detecting a selected stimulus as disclosed above, wherein the second probe molecule is an antibody capable of binding the first probe nucleic acid when it is chemically or enzymatically modified.

In some embodiments of the present disclosure, the structure for detecting a selected stimulus as disclosed above, wherein the one or more functional molecules comprise a first protein and a second protein, the first protein being a transmembrane receptor capable of binding at least one type of ligand and the second protein capable of binding the first protein when the first protein is bound by the at least one type of ligand, the first protein bound to the first shape inside surface and the second protein bound to the second shape inside surface, and the binding of the first protein to the second protein actuates the bistable molecular sensor from the opened state to the closed state.

In some embodiments of the present disclosure, the structure for detecting a selected stimulus as disclosed above, wherein the first protein is bound to the first shape inside surface using a binding moiety selected from: a linker molecule conjugated to the first protein and bound to directly or indirectly to the first shape inside surface and a protein-lipid nanodisc or a DNA-lipid nanodisc including the first protein and bound to the first shape inside surface.

In some embodiments of the present disclosure, the structure for detecting a selected stimulus as disclosed above, further comprising a third protein, wherein the first protein is a G-protein coupled receptor (GPCR), the second protein is beta-arrestin, and the third protein is a soluble or polynucleotide platform-bound G-protein receptor kinase (GRK), and wherein the beta-arrestin is capable of binding the GPCR if GRK has phosphorylated the ligand-bound GPCR, thereby actuating the bistable molecular sensor from the opened state to the closed state.

In some embodiments of the present disclosure, the structure for detecting a selected stimulus as disclosed above, wherein: the target molecule is a target ligand, the one or more functional molecules include a DNA or RNA riboswitch capable of binding the target ligand and a probe molecule including a DNA sequence or an RNA sequence or a protein capable of binding the DNA or RNA riboswitch when bound to the ligand, the DNA or RNA riboswitch bound to the first shape inside surface and the probe molecule bound to the second shape inside surface, and the binding of the probe molecule to the DNA or RNA riboswitch actuates the bistable molecular sensor from the opened state to the closed state.

In some embodiments of the present disclosure, the structure for detecting a selected stimulus as disclosed above, wherein the target molecule is a chemical or enzymatic agent, the one or more functional molecules is a single molecule selected from a protein or a nucleic acid capable of being cleaved by the chemical or enzymatic agent, the single molecule attached to both the first shape inside surface and the second shape inside surface, and the cleaving of the single molecule in the presence of the target molecule actuates the bistable molecular sensor from the closed state to the opened state.

In some embodiments of the present disclosure, the structure for detecting a selected stimulus as disclosed above, wherein the one or more functional molecules include a first molecule and a second molecule, the first molecule capable of binding the second molecule upon modification of the first and/or the second molecule in the presence of a selected stimulus, the first molecule bound to the first shape inside surface and the second molecule bound to the second shape inside surface, and the binding of the first molecule to the second molecule actuates the bistable molecular sensor from the closed state to the opened state.

In some embodiments of the present disclosure, the structure for detecting a selected stimulus as disclosed above, wherein the first molecule and the second molecule are selected from a first protein and a second protein or a first nucleic acid and a second nucleic acid, the selected stimulus is selected from a chemical agent, an enzyme, temperature, light, acidity (pH), and/or ionic state, and the modification is selected from a chemical modification, enzymatic modification, or a conformational or structural change in one of the first molecule or the second molecule as a result of the presence of or a change in the temperature, the light, the pH, or the ionic conditions.

In some embodiments of the present disclosure, the structure for detecting a selected stimulus as disclosed above, wherein the substrate surface includes one or more electrodes and the non-immobilized first shape or the non-immobilized second shape comprises a working electrode, working electrode having a surface selected from gold, platinum, graphene, indium oxide, or indium tin oxide, and the non-immobilized first shape or the non-immobilized second shape comprising a label of one or more redox active molecules selected from methylene blue, ferrocene, or 1,3-diaza-2-oxophenothiazine (tC, a tricyclic cytosine analog), and wherein the redox active molecules and the working surface electrode produces an electron transfer rate wherein the electron transfer rate is a closed electron transfer rate when the bistable molecular sensor is in the closed state and is an open electron transfer rate when the bistable molecular sensor is in the opened state.

In some embodiments of the present disclosure, the structure for detecting a selected stimulus as disclosed above, further comprising a reference electrode and a counter electrode, wherein: the electron transfer rate is detected using square wave voltammetry, the working electrode surface is e-beam deposited or template-stripped gold, the non-immobilized first shape or the non-immobilized second shape is labeled with one or more methylene blue molecules, the immobilized first shape or the immobilized second shape is coated with an alkanethiol self-assembled monolayer, the reference electrode is a silver/silver chloride electrode, and the counter electrode is a platinum wire positioned about the substrate surface.

In some embodiments of the present disclosure, the structure for detecting a selected stimulus as disclosed above, wherein the immobile polynucleotide shape adheres to the gold via thiol modifications on the polynucleotide shape.

In some embodiments of the present disclosure, the structure for detecting a selected stimulus as disclosed above, wherein the immobile polynucleotide shape adheres to the gold via single-stranded polyadenosine strands.

In some embodiments of the present disclosure, the structure for detecting a selected stimulus as disclosed above, wherein the immobile polynucleotide shape adheres to the gold via phosphorothioate modifications to the polynucleotide background.

In some embodiments of the present disclosure, the structure for detecting a selected stimulus as disclosed above, wherein the mobile polynucleotide shape is rendered nonadherent for the background with polyethylene glycol modifications.

In some embodiments of the present disclosure, the structure for detecting a selected stimulus as disclosed above, wherein the non-immobilized first shape or the non-immobilized second shape is rendered nonadherent for the background with dextran modifications.

In some embodiments of the present disclosure, the structure for detecting a selected stimulus as disclosed above, wherein the non-immobilized first shape or the non-immobilized second shape is rendered nonadherent with thiolated polyethylene glycol molecules.

In some embodiments of the present disclosure, the structure for detecting a selected stimulus as disclosed above, wherein the non-immobilized first shape or the non-immobilized second shape is a rigid 2D plate and wherein the redox molecules are uniformly distributed on the plate, and wherein the immobile shape is between the redox molecules and the surface.

In some embodiments of the present disclosure, the structure for detecting a selected stimulus as disclosed above, wherein the non-immobilized first shape or the non-immobilized second shape is a rigid 2D plate, and wherein the immobile polynucleotide shape is a plate with window or hole which allows direct access to the surface, and wherein the redox molecules on the mobile shape are positioned so that they are directly over the window when the sensor is in the closed state.

In some embodiments of the present disclosure, the structure for detecting a selected stimulus as disclosed above, wherein the non-immobilized first shape or the non-immobilized second shape is a rigid 3D shape with a rigid arm, and wherein the redox molecules are positioned at the end of the rigid arm so that they extend outside the area of the immobile polynucleotide shape and wherein the redox molecules are positioned directly over the surface in when the sensor is in the closed state.

In some embodiments of the present disclosure, the structure for detecting a selected stimulus as disclosed above, wherein the non-immobilized first shape or the non-immobilized second shape is a rigid hemisphere or dome, and wherein the redox molecules are along the edge of the hemisphere, so that they extend outside the area of the immobile polynucleotide shape, and wherein the redox molecules are positioned directly over the surface in when the sensor is in the closed state.

In some embodiments of the present disclosure, the structure for detecting a selected stimulus as disclosed above, wherein: the mechanism of detection is field effect sensing on the surface of one or more transistors, the surface on which immobilized first shape or the immobilized second shape is bound directly to a 1D or 2D gate material selected from carbon nanotubes, silicon nanowires, graphene, indium oxide, or molybdenum disulfide, the bulk liquid above the surface acts as the gate of a transistor, and the current or voltage response between a solution counter electrode and the surface working electrode changes when the bistable molecular sensor is actuated between opened and closed states.

In some embodiments of the present disclosure, the structure for detecting a selected stimulus as disclosed above, wherein the surface on which the immobile polynucleotide shape is bound to graphene, and wherein the immobile polynucleotide shape is adhered to the graphene via single-stranded DNA extensions.

In some embodiments of the present disclosure, the structure for detecting a selected stimulus as disclosed above, wherein the surface on which the immobile polynucleotide shape is bound to graphene, and wherein the graphene surface is coated and rendered negative with a pyrene carboxylic acid, and wherein the immobile polynucleotide shape is adhered to the surface via electrostatic interactions between divalent magnesium ions and the carboxylic acid coating.

In some embodiments of the present disclosure, the structure for detecting a selected stimulus as disclosed above, wherein the surface on which the immobile polynucleotide shape is bound to graphene, and wherein the graphene surface is coated and rendered positive with polylysine, and wherein the immobile polynucleotide shape is adhered to the graphene via electrostatic interactions with the positively charged polylysine coating.

In some embodiments of the present disclosure, the structure for detecting a selected stimulus as disclosed above, wherein the surface on which the immobile polynucleotide shape is bound to graphene, wherein the mobile polynucleotide shape is rendered nonadherent for the background with polyethylene glycol modifications.

In some embodiments of the present disclosure, the structure for detecting a selected stimulus as disclosed above, wherein the surface on which the immobile polynucleotide shape is bound to graphene, and wherein the background is rendered nonadherent for the mobile polynucleotide shape by a coating of polylysine-graft-polyethylene glycol polymers.

In some embodiments of the present disclosure, the structure for detecting a selected stimulus as disclosed above, wherein the surface on which the immobile polynucleotide shape is bound is indium oxide, wherein the indium oxide has been rendered adherent for the immobile polynucleotide shape by oxygen plasma treatment, wherein magnesium ions are used to bridge between the surface and the polynucleotide shape.

In some embodiments of the present disclosure, the structure for detecting a selected stimulus as disclosed above, wherein the surface on which the immobile polynucleotide shape is bound is indium oxide, wherein the indium oxide has been rendered adherent for the immobile polynucleotide shape by treatment with a carboxysilanes, wherein magnesium ions are used to bridge between the surface and the polynucleotide shape.

In some embodiments of the present disclosure, the structure for detecting a selected stimulus as disclosed above, wherein the surface on which the immobile polynucleotide shape is bound is indium oxide, wherein the background has been rendered nonadherent for the mobile polynucleotide shape by silanization with trimethyl silyl groups via vapor deposition of hexamethyldisilazane.

In some embodiments of the present disclosure, the structure for detecting a selected stimulus as disclosed above, wherein the surface on which the immobile polynucleotide shape is bound is indium oxide, wherein the background has been rendered nonadherent for the mobile polynucleotide shape by silanization with a polyethylene glycol (PEG) silane.

In some embodiments of the present disclosure, the structure for detecting a selected stimulus as disclosed above, wherein the mobile polynucleotide shape is a rigid 2D plate, and wherein the polynucleotide material of the mobile shape is a roughly constant distance from the gate in the closed state, and wherein the immobile shape lies between the mobile shape and the gate material surface.

In some embodiments of the present disclosure, the structure for detecting a selected stimulus as disclosed above, wherein the mobile polynucleotide shape is a rigid 2D plate, and wherein the immobile polynucleotide shape is a plate with window or hole which allows direct access to the surface, specifically so that there is no material of the immobile polynucleotide shape between the mobile shape and the gate material surface when the sensor is in the closed state.

In some embodiments of the present disclosure, the structure for detecting a selected stimulus as disclosed above, wherein the mobile polynucleotide shape is a rigid 3D shape with a rigid arm, and wherein the end of the rigid arm extends outside the area of the immobile polynucleotide shape, specifically so that there is no material of the immobile polynucleotide shape between the mobile shape and the gate material surface when the sensor is in the closed state.

In some embodiments of the present disclosure, the structure for detecting a selected stimulus as disclosed above, wherein the mobile polynucleotide shape is a rigid hemisphere or dome, and wherein the edge of the hemisphere extends outside the area of the immobile polynucleotide shape, specifically so that there is no material of the immobile polynucleotide shape between the mobile shape and the gate material surface when the sensor is in the closed state.

In some embodiments of the present disclosure, the structure for detecting a selected stimulus as disclosed above, wherein the mechanism of detection is field effect sensing on the surface of one or more transistors, and the surface on which the immobile polynucleotide shape is bound to a dielectric capping layer material selected from silicon dioxide, aluminum oxide, or silicon nitride and wherein underneath the capping layer is a semiconductor gate selected from doped silicon, or zinc oxide, wherein the bulk liquid above the surface acts as the gate of a transistor, and wherein the current or voltage response between a working solution electrode and the surface changes when the sensor switches between open and closed states.

In some embodiments of the present disclosure, the structure for detecting a selected stimulus as disclosed above, wherein the capping layer has been rendered adherent for the immobile polynucleotide shape by oxygen plasma treatment, wherein magnesium ions are used to bridge between the surface and the polynucleotide shape.

In some embodiments of the present disclosure, the structure for detecting a selected stimulus as disclosed above, wherein the capping layer has been rendered adherent for the immobile polynucleotide shape by treatment with a carboxysilanes, wherein magnesium ions are used to bridge between the surface and the polynucleotide shape.

In some embodiments of the present disclosure, the structure for detecting a selected stimulus as disclosed above, wherein the background has been rendered nonadherent for the mobile polynucleotide shape by silanization with trimethyl silyl groups via vapor deposition of hexamethyldisilazane.

In some embodiments of the present disclosure, the structure for detecting a selected stimulus as disclosed above, wherein the background has been rendered nonadherent for the mobile polynucleotide shape by silanization with a polyethylene glycol (PEG) silane.

In some embodiments of the present disclosure, the structure for detecting a selected stimulus as disclosed above, wherein the mobile polynucleotide shape is a rigid 2D plate, and wherein the polynucleotide material of the mobile shape is a roughly constant distance from the capping layer in the closed state, and wherein the immobile shape lies between the mobile shape and the gate material surface.

In some embodiments of the present disclosure, the structure for detecting a selected stimulus as disclosed above, wherein the mobile polynucleotide shape is a rigid 2D plate, and wherein the immobile polynucleotide shape is a plate with window or hole which allows direct access to the surface, specifically so that there is no material of the immobile polynucleotide shape between the mobile shape and the capping layer surface when the sensor is in the closed state.

In some embodiments of the present disclosure, the structure for detecting a selected stimulus as disclosed above, wherein the mobile polynucleotide shape is a rigid 3D shape with a rigid arm, and wherein the end of the rigid arm extends outside the area of the immobile polynucleotide shape, specifically so that there is no material of the immobile polynucleotide shape between the mobile shape and the capping layer surface when the sensor is in the closed state.

In some embodiments of the present disclosure, the structure for detecting a selected stimulus as disclosed above, wherein the mobile polynucleotide shape is a rigid hemisphere or dome, and wherein the edge of the hemisphere extends outside the area of the immobile polynucleotide shape, specifically so that there is no material of the immobile polynucleotide shape between the mobile shape and the gate material surface when the sensor is in the closed state.

In some embodiments of the present disclosure, a structure for detecting a selected stimulus or target molecule in a solution is provided, the structure including a bistable molecular sensor including: a polynucleotide platform forming a first shape and a second shape, the first shape connected to the second shape by a linker, the polynucleotide platform having an open state and a closed state, the open state including the first shape and the second shape being apart from each other by at least a first distance and the closed state comprising the first shape and the second shape being at or less than a second distance from each other; and one or more functional molecules bound to the first shape and/or the second shape, the one or more functional molecules capable of actuating the bistable molecular sensor from the open state to the closed state in the presence of a selected stimulus.

In some embodiments of the present disclosure, the structure for detecting a selected stimulus as disclosed above, wherein the polynucleotide platform is selected from a scaffolded deoxyribonucleic acid (DNA) origami, scaffolded ribonucleic acid (RNA) origami, scaffolded hybrid DNA:RNA origami, single-stranded DNA tiles, multi-stranded DNA tiles; single-stranded RNA origami, multi-stranded RNA tiles, or a hierarchically composed DNA or RNA origami with multiple scaffolds.

In some embodiments of the present disclosure, the structure for detecting a selected stimulus as disclosed above, wherein the first shape is labelled with one or more luminescent compounds selected from a europium chelate or a terbium chelate, the second shape is labelled with a fluorescent organic dye or quantum dots, and the actuating of the bistable molecular sensor from the opened state to the closed state generates a detectable Luminescence Resonance Energy transfer (LRET).

In some embodiments of the present disclosure, the structure for detecting a selected stimulus as disclosed above, wherein the first shape includes a first shape inside surface and a first shape outside surface and the second shape includes a second shape inside surface and a second shape outside surface and the one or more functional molecules are bound to the first shape inside surface and/or the second shape inside surface, the first shape inside surface facing the second shape inside surface.

In some embodiments of the present disclosure, the structure for detecting a selected stimulus as disclosed above, wherein the one or more functional molecules include: a nucleotide barcode on the first shape outside surface or the second shape outside surface; an affinity tag on the first shape inside surface or the second shape inside surface; and a first binding molecule and a second binding molecule both capable of binding the target molecule, the first binding molecule on the first shape inside surface and the second binding molecule on the second shape inside surface, the binding of the target molecule to the first and second binding molecules capable of actuating the bistable molecular sensor from the open state to the closed state thereby sterically blocking the affinity tag.

In some embodiments of the present disclosure, a detection system including a plurality of the structures of claim 100, the plurality of structures including a plurality of bistable molecular sensors each of which is capable of detecting a different target molecule, the nucleotide barcode on each of the plurality of bistable molecular sensors being unique for each of the different target molecules, wherein each of the plurality of bistable molecular sensors when not bound to a target molecule are in the opened state and are capable of being separated out of the sample solution by binding the affinity tag and the closed state bistable molecular sensors remain in solution and are capable of being identified by the unique nucleotide barcode.

In some embodiments of the present disclosure, the structure for detecting a selected stimulus as disclosed above, wherein the plurality of structures include at least 8 different bistable molecular sensors capable of binding at least 8 different target molecules and having at least 8 unique nucleotide barcodes capable of being identified by quantitative PCR.

In some embodiments of the present disclosure, the structure for detecting a selected stimulus as disclosed above, wherein the plurality of structures includes at least 1,000 different bistable molecular sensors capable of binding at least 1,000 different target molecules and having at least 1,000 unique nucleotide barcodes capable of being identified by next generation sequencing.

In some embodiments of the present disclosure, the structure for detecting a selected stimulus as disclosed above, wherein the unique nucleotide barcode includes a restriction site sequence and is capable of being cleaved from the first shape outside surface and/or the second shape outside surface by cleavage at the restriction site.

In some embodiments of the present disclosure, the structure for detecting a selected stimulus as disclosed above, wherein the unique nucleotide barcode includes a complex capable of strand displacement and is capable of being released from the first shape outside surface and/or the second shape outside surface by addition of a DNA or RNA strand.

In some embodiments of the present disclosure, the structure for detecting a selected stimulus as disclosed above, wherein the polynucleotide platform is selected from scaffolded deoxyribonucleic acid (DNA) origami, scaffolded ribonucleic acid (RNA) origami, scaffolded hybrid DNA:RNA origami, single-stranded DNA tiles, multi-stranded DNA tiles, single-stranded RNA origami, multi-stranded RNA tiles, or hierarchically composed DNA or RNA origami with multiple scaffolds.

In some embodiments of the present disclosure, the structure for detecting a selected stimulus as disclosed above, wherein the selected stimulus is a target molecule.

In some embodiments of the present disclosure, the structure for detecting a selected stimulus as disclosed above, wherein the one or more functional molecules include a first antibody and a second antibody, the first antibody capable of binding a first epitope on the target molecule and the second antibody capable of binding a second epitope on the target molecule, the first epitope being different from the second epitope.

In some embodiments of the present disclosure, the structure for detecting a selected stimulus as disclosed above, wherein one or more of the first antibody are bound to the first shape inside surface, one or more of the second antibody are bound to the second shape inside surface, and the binding of the target molecule to the first antibody and the second antibody actuates the bistable molecular sensor from the opened state to the closed state.

In some embodiments of the present disclosure, the structure for detecting a selected stimulus as disclosed above, wherein: the target molecule is a target single-stranded nucleic acid, the one or more functional molecules include a first probe single-stranded nucleic acid and a second probe single-stranded nucleic acid each of which are complementary to a different region of the target single-stranded nucleic acid, the first probe single-stranded nucleic acid bound to the first shape inside surface and the second probe single-stranded nucleic acid bound to the second shape inside surface, and the binding of the target single-stranded nucleic acid to the first probe single-stranded nucleic acid and the second probe single-stranded nucleic acid is capable of actuating the bistable molecular sensor from the opened state to the closed state.

In some embodiments of the present disclosure, the structure for detecting a selected stimulus as disclosed above, wherein: the target molecule is a target double-stranded nucleic acid, the one or more functional molecules include a first endonuclease and guide RNA (gRNA) complex and a second endonuclease and gRNA complex each of which is capable of binding a different region of the target double-stranded nucleic acid, the first endonuclease and gRNA complex bound to the first shape inside surface and the second endonuclease and gRNA complex bound to the second shape inside surface, and the binding of the target double-stranded nucleic acid to the first endonuclease and gRNA complex and the second endonuclease and gRNA complex actuates the bistable molecular sensor from the opened state to the closed state.

In some embodiments of the present disclosure, the structure for detecting a selected stimulus as disclosed above, wherein: the target molecule is a target double-stranded nucleic acid, the one or more functional molecules include an allosteric endonuclease and gRNA complex comprising a hidden nucleotide region and a probe nucleotide complementary to the hidden nucleotide, the allosteric endonuclease and gRNA complex bound to the first shape inside surface and the probe nucleotide bound to the second shape inside surface, and the binding of the target double-stranded nucleic acid to the allosteric endonuclease and gRNA complex presents the hidden nucleotide region for binding with the probe nucleotide thereby actuating the bistable molecular sensor from the opened state to the closed state.

In some embodiments of the present disclosure, the structure for detecting a selected stimulus as disclosed above, wherein the one or more functional molecules comprise a competitor for the target molecule and an antibody capable of binding the target molecule and the competitor, the competitor being bound to the first shape inside surface and the antibody being bound the second shape inside surface, wherein in the absence of the target molecule, the competitor binds to the antibody and in the presence of the target molecule, the competitor is displaced and actuates the bistable molecular sensor from the closed state to the opened state.

In some embodiments of the present disclosure, the structure for detecting a selected stimulus as disclosed above, wherein the one or more functional molecules include a first protein and a second protein, the first protein capable of being chemically or enzymatically modified by the target molecule, the second protein capable of binding the first protein when it is chemically or enzymatically modified, the first protein bound to the first shape inside surface and the second protein bound to the second shape inside surface, and the binding of the first protein to the second protein actuates the bistable molecular sensor from the opened state to the closed state.

In some embodiments of the present disclosure, the structure for detecting a selected stimulus as disclosed above, wherein the chemical or enzymatic modification of the first protein is selected from phosphorylation, acetylation, ubiquitination, prenylation, adenylylation, or glycosylation.

In some embodiments of the present disclosure, the structure for detecting a selected stimulus as disclosed above, wherein the second protein is a naturally occurring protein.

In some embodiments of the present disclosure, the structure for detecting a selected stimulus as disclosed above, wherein the second protein is an antibody capable of selectively binding the first protein when it is chemically or enzymatically modified.

In some embodiments of the present disclosure, the structure for detecting a selected stimulus as disclosed above, wherein the one or more functional molecules comprise a first probe nucleic acid and a first probe molecule, the first probe nucleic acid capable of being chemically or enzymatically modified and the second probe molecule capable of binding the first probe nucleic acid when the first probe nucleic acid is chemically or enzymatically modified, the first probe nucleic acid bound to the first shape inside surface and the second probe molecule bound to the second shape inside surface, and the binding of the first probe nucleic acid to the second probe molecule actuates the bistable molecular sensor from the opened state to the closed state.

In some embodiments of the present disclosure, the structure for detecting a selected stimulus as disclosed above, wherein the chemical or enzymatic modification of the first probe nucleic acid is selected from cytosine methylation, cytosine hydroxymethylation, cytosine formylation, cytosine carboxylation, adenosine methylation, alkylation, or thymine dimerization.

In some embodiments of the present disclosure, the structure for detecting a selected stimulus as disclosed above, wherein the second probe molecule is a naturally-occurring molecule.

In some embodiments of the present disclosure, the structure for detecting a selected stimulus as disclosed above, wherein the second probe molecule is an antibody capable of binding the first probe nucleic acid when it is chemically or enzymatically modified.

In some embodiments of the present disclosure, the structure for detecting a selected stimulus as disclosed above, wherein the one or more functional molecules include a first protein and a second protein, the first protein being a transmembrane receptor capable of binding at least one type of ligand and the second protein capable of binding the first protein when the first protein is bound by the at least one type of ligand, the first protein bound to the first shape inside surface and the second protein bound to the second shape inside surface, and the binding of the first protein to the second protein actuates the bistable molecular sensor from the opened state to the closed state.

In some embodiments of the present disclosure, the structure for detecting a selected stimulus as disclosed above, wherein the first protein is bound to the first shape inside surface using a binding moiety selected from: a linker molecule conjugated to the first protein and bound to directly or indirectly to the first shape inside surface, and a protein-lipid nanodisc or a DNA-lipid nanodisc including the first protein and bound to the first shape inside surface.

In some embodiments of the present disclosure, the structure for detecting a selected stimulus as disclosed above, further comprising a third protein, wherein the first protein is a G-protein coupled receptor (GPCR), the second protein is beta-arrestin, and the third protein is a soluble or polynucleotide platform-bound G-protein receptor kinase (GRK), and wherein the beta-arrestin is capable of binding the GPCR if GRK has phosphorylated the ligand-bound GPCR, thereby actuating the bistable molecular sensor from the opened state to the closed state.

In some embodiments of the present disclosure, the structure for detecting a selected stimulus as disclosed above, wherein the target molecule is a target ligand, the one or more functional molecules include a DNA or RNA riboswitch capable of binding the target ligand and a probe molecule including a DNA sequence or an RNA sequence or a protein capable of binding the DNA or RNA riboswitch when bound to the ligand, the DNA or RNA riboswitch bound to the first shape inside surface and the probe molecule bound to the second shape inside surface, and the binding of the probe molecule to the DNA or RNA riboswitch actuates the bistable molecular sensor from the opened state to the closed state.

In some embodiments of the present disclosure, the structure for detecting a selected stimulus as disclosed above, wherein the target molecule is a chemical or enzymatic agent, the one or more functional molecules is a single molecule selected from a protein or a nucleic acid capable of being cleaved by the chemical or enzymatic agent, the single molecule attached to both the first shape inside surface and the second shape inside surface, and the cleaving of the single molecule in the presence of the target molecule actuates the bistable molecular sensor from the closed state to the opened state.

In some embodiments of the present disclosure, the structure for detecting a selected stimulus as disclosed above, wherein the one or more functional molecules include a first molecule and a second molecule, the first molecule capable of binding the second molecule upon modification of the first and/or the second molecule in the presence of a selected stimulus, the first molecule bound to the first shape inside surface and the second molecule bound to the second shape inside surface, and the binding of the first molecule to the second molecule actuates the bistable molecular sensor from the closed state to the opened state.

In some embodiments of the present disclosure, a detection system comprising a plurality of the structures as disclosed herein, the plurality of structures including a plurality of different bistable molecular sensors each corresponding to a different selected stimulus or target molecule, the plurality of bistable molecular sensors being positioned in a selected plurality of regions on an optically detectable substrate surface selected from ink jet printing or microarray printing and wherein multiple copies of each of the different plurality of bistable sensors are bound to each of the selected plurality of regions, wherein the plurality of different bistable molecular sensors comprise up to 1,000 different bistable molecular sensors and the selected plurality of regions comprise up to 1,000 regions.

In some embodiments of the present disclosure, the structure for detecting a selected stimulus as disclosed above, wherein each of the up to 1000 regions is lithographically patterned and each is divided into at least 10 discrete single-molecule binding sites for DNA origami placement prior to, wherein each one of said binding sites is filled by exactly one bistable molecular sensor with at least 80% probability and wherein a single-molecule measurements of the opened or closed state of the bistable molecular sensor includes total internal reflectance spectroscopy on a transparent substrate, quenching of fluorescence by a gold substrate, quenching of fluorescence by a graphene substrate, or enhancement of fluorescence by an optical bowtie lithographically patterned proximal to the binding site.

In some embodiments of the present disclosure, a detection system including a plurality of the structures as disclosed herein, wherein up to 4000 distinct bistable sensors for different analytes are spotted onto substrate suitable for electronic detection using one of: jet printing or microarray printing and wherein each spot is positioned over a distinct electronic sensor being one of: a working electrochemical electrode composed of gold, a working electrochemical electrode composed of graphene, a working electrochemical electrode composed of platinum, an electrochemical sensor built using CMOS, a field effect sensor composed of graphene, a field effect sensor composed of indium oxide, a field effect sensor composed of molybdenum disulfide, a field effect sensor composed of carbon nanotubes, a field effect sensor composed of silicon nanowires, or a silicon-based field-effect transistor.

In some embodiments of the present disclosure, the detection system for detecting a selected stimulus as disclosed above, wherein DNA origami placement is used to position a bistable device at a binding site between electrodes spaced less than 100 nanometers apart, and wherein single-molecule electrochemical measurements distinguishing open and closed states are made via redox cycling.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, together with the specification, illustrate exemplary embodiments of the present invention, and, together with the description, serve to explain the principles of the present invention.

DETAILED DESCRIPTION

Figure 1A:
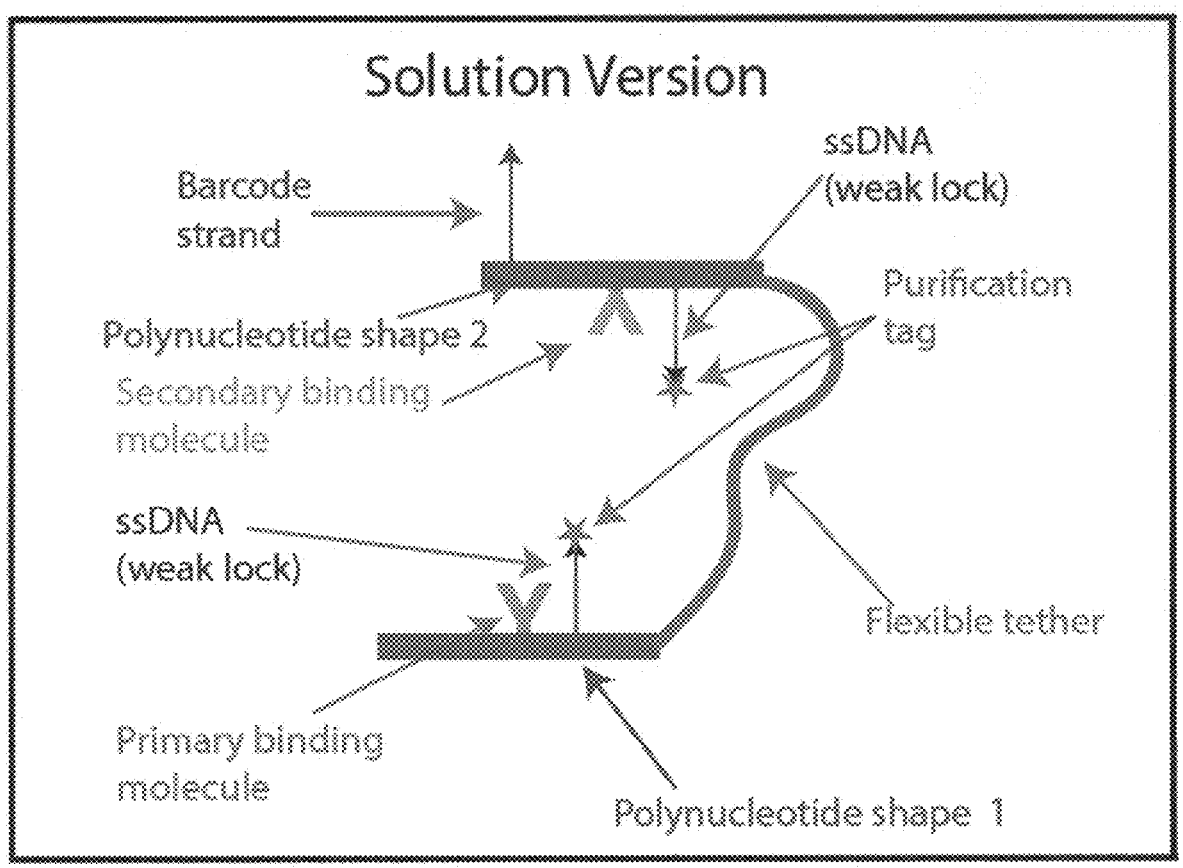
FIG. 1A is a schematic of the bistable molecular sensor, designed to work in solution, which includes both an affinity tag and a DNA barcode.

In the following detailed description, only certain exemplary embodiments of the present invention are shown and described, by way of illustration. As those skilled in the art would recognize, the invention may be embodied in many different forms and should not be construed as being limited to the embodiments set forth herein.

Aspects of embodiments of the present invention relate to bistable molecular sensors created using a polynucleotide platform (e.g., a general architecture for the generation of well-defined two-dimensional or three-dimensional shapes from polynucleotides) onto substrates. Polynucleotideplatforms include but are not limited to scaffolded deoxyribonucleic acid (DNA) origami (Rothemund, Paul W K. "Folding DNA to create nanoscale shapes and patterns", Nature 440.7082 (2006): 297), scaffolded ribonucleic (RNA) origami (Torelli, Emanuela et al, "Isothermal folding of a light-up bio-orthogonal RNA origami nanoribbon", Scientific Reports 8 (2018): 6989), scaffolded hybrid DNA:RNA origami (Wang, Pengfei, et al. "RNA-DNA hybrid origami: folding of a long RNA single strand into complex nanostructures using short DNA helper strands", Chemical Communications 49 (2013) 5462-5464), scaffold-free DNA single-stranded tile (DNA brick) systems (Wei, Bryan, et al., "Complex shapes self-assembled from single-stranded DNA tiles", Nature 485 (2012):623-626 and Ke, Yonggang, et al., "Three-Dimensional Structures Self-Assembled from DNA Bricks", Science 338 (2012):1177-1183), scaffold-free multi-stranded DNA tile systems (Winfree, Erik, et al., "Design and self-assembly of two-dimensional DNA crystals", Nature 394 (1998) 539-44) or RNA tile systems (Chworos, Arkadiusz, et al., "Building programmable jigsaw puzzles with RNA." Science 306 (2004):2068-72), intramolecularly-folded single-stranded RNA (Geary, Cody, et al., "A single-stranded architecture for cotranscriptional folding of RNA nanostructures", Science 345 (2014) 799-804) or single-stranded DNA origami (Han, Dongran, et al., "Single-stranded DNA and RNA origami", Science 358 (2017): eaao2648), all of which are incorporated by reference in their entirety. For the sake of clarity, aspects of embodiments of the present invention will be described herein primarily in the context of scaffolded DNA origami as a particular instance of a "molecular shape." However, embodiments of the present invention are not limited to scaffolded DNA origami. Instead, embodiments of the present invention include molecular shapes made using other polynucleotide platforms, such as the platforms listed above, where some examples of applications of embodiments of the present invention to other polynucleotide platforms are described in more detail below.

Some embodiments of the present invention have two parts: first, a bistable polynucleotide sensor that is designed to change its state upon application of an external stimulus, such as a solution of analyte molecules, and second a set of protocols and methods which enable the state change of the device to be recorded as either a DNA sequence, an optical signal, or an electronic signal.

Figure 1B:
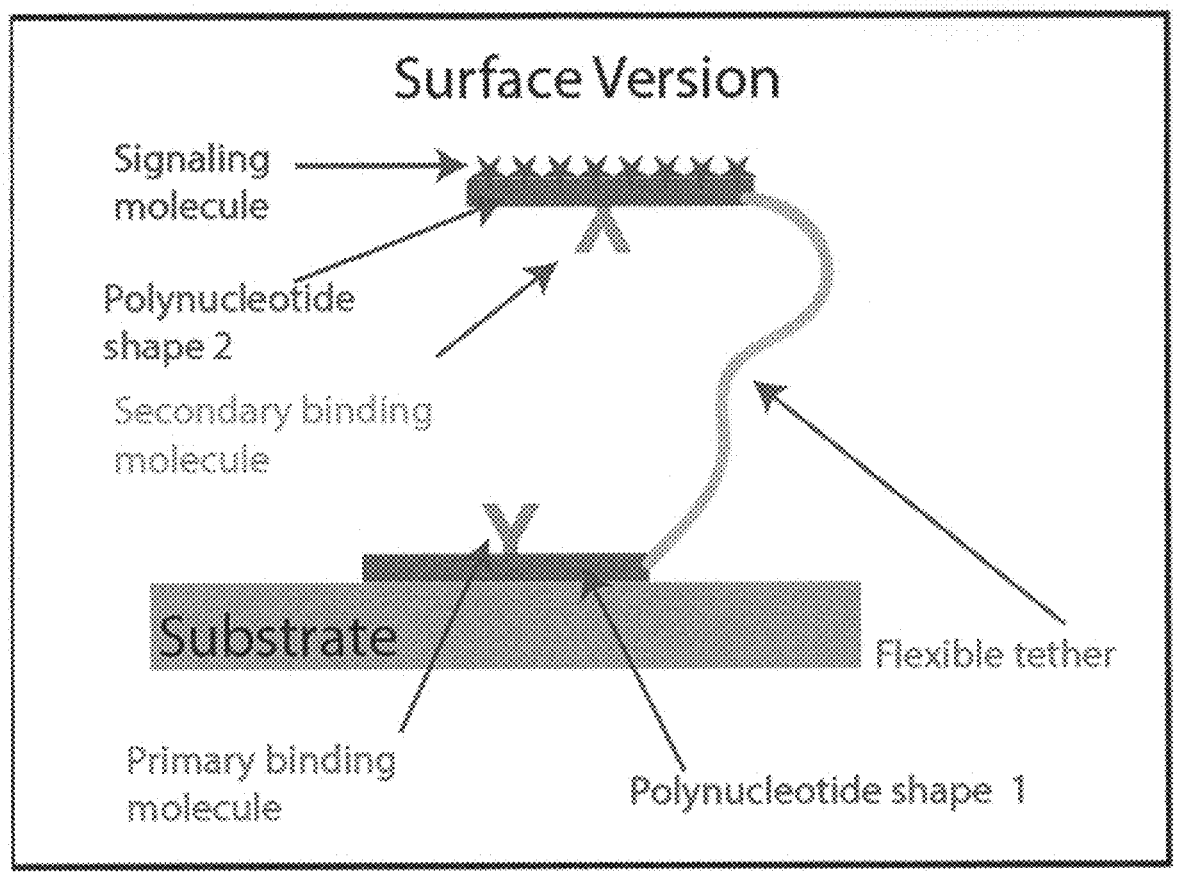
FIG. 1B is a schematic of the bistable molecular sensor that is composed of two polynucleotide shapes, one of which is immobilized on a surface, tethered by a flexible linker, suitable for optical or electronic detection.

Described herein are bistable polynucleotide sensors that can function in solution (FIG. 1A) or on a surface (FIG. 1B). For purposes of introducing bistable polynucleotide sensors, features common to both solution and surface versions are first described. In a embodiment, the bistable polynucleotide sensor is composed of two polynucleotide shapes, tethered together by one or more flexible linkers. For clarity, only a single linker is depicted in FIG. 1.

Bistable polynucleotide sensors represent a general platform for detecting molecular events. For clarity, sensors as depicted in FIGS. 1A-1B where these sensors adapted for the detection of binding events, a capability which is commonly used to measure the concentration of analyte molecules. Further, FIGS. 1A-1B depicts such sensors as adapted specifically for use with pairs of antibodies in a "sandwich actuation mode" for the detection of proteins, a capability which is commonly used in sandwich immunoassays such as ELISA. Later, FIG. 3 depicts sandwich actuation mode for the detection of nucleic acids. Still later, FIGS. 4 and 5 depict a number of embodiments which highlight some of the other molecular events which can be detected and quantified using the platform, and details regarding the various molecular entities involved.

Accordingly, two illustrative examples of the sandwich actuation mechanism (FIG. 1A, "Solution Version", and FIG. 1B "Surface Version"), each of the polynucleotide shapes carry a "binding molecule" (e.g. aptamer or antibody) that binds a unique non-overlapping region of the analyte molecule or particle. In the absence of the target analyte the two origami move relative to each other via the flexible linker, a state which is referred to as "open". Upon capturing the analyte, however, the two origami bind to form a single semi-rigid unit, a state which is referred to as "closed". In some embodiments, at least one of the origami carries a unique DNA barcode or light-emitting or electronically-active signaling molecules that can used to detect the state change from open to closed. For the purposes of clarity, in the description of one embodiment of the solution version in FIG. 1A, the possibility that one or both of the polynucleotide shapes carry light-emitting molecules has been omitted; however, in some embodiments, the solution version carry light emitting molecules for the purposes of signal detection are as described below.

The following terms are used interchangeably throughout this disclosure: bistable molecular sensor, bistable sensor, bistable detector, bistable device, bistable polynucleotide nanostructure, bistable polynucleotide device, bistable polynucleotide sensor, flytrap sensor, flytrap detector, or flytrap.

In this disclosure, reference is made to the two at least semi-rigid polynucleotide shapes of the bistable sensor as "lids", and may refer to a "top lid" and a "bottom lid" either in reference to the orientation of these lids within a diagram, or with respect to the orientation of a bistable sensor on a surface. These lids are "DNA origami" when they may be implemented using any polynucleotide platform as described above.

In this disclosure, the flexible connection between the lids as a "linker", or "hinge". In some embodiments there may be more than one linker between the lids, and in some embodiments a single linker may be comprised of a single-stranded DNA, double-stranded DNA, single-stranded RNA, double-stranded RNA, a bundle of double-stranded DNA helices, a bundle of double-stranded RNA helices, polynucleotide analogs, or a non-polynucleotide polymer such as polyethylene glycol (PEG). Depending on the embodiment, linkers may vary in length from a single covalent bond (~2 angstroms), up to a 10,000 nucleotide double-stranded linker (~3.5 microns). Embodiments using solution based detection (e.g. but not limited to LRET or PCR-amplifiable DNA signals) will typically use shorter linkers (1 nm to 10 nm) whereas embodiments using surface-based optical detection or electronic detection will typically use longer linkers (10 nm to 4 microns).

While some embodiments of the bistable polynucleotide sensor comprise two independently-folded DNA origami shapes self-assembled with an independently-synthesized linker, other embodiments comprise a single DNA origami wherein both polynucleotide shapes and the linker are all folded from a single long DNA scaffold strand. Still other embodiments of the bistable sensor are created from single-stranded DNA tiles, from multi-stranded DNA tiles, from single-stranded RNA or DNA origami, or any other suitable polynucleotide platform.

Depending on the embodiment, the state change induced by a molecular event (such as the binding of an analyte molecule) may be detected either in a solution or on a surface by one of several different methods, including but not limited to: (1) If the assay is performed in solution, then the state change (open versus closed) may be detected either via a unique DNA barcode which encodes the identity of the analyte being quantified or via Luminescence Resonance Energy Transfer, or (2) If the assay is performed on a surface, then the state change maybe be recorded as a change in either an optical or electrical signal, where the spatial position of the bistable origami device on the surface encodes the nature of the molecular event being recorded (e.g. the identity of the analyte being quantified).

Figure 2A:
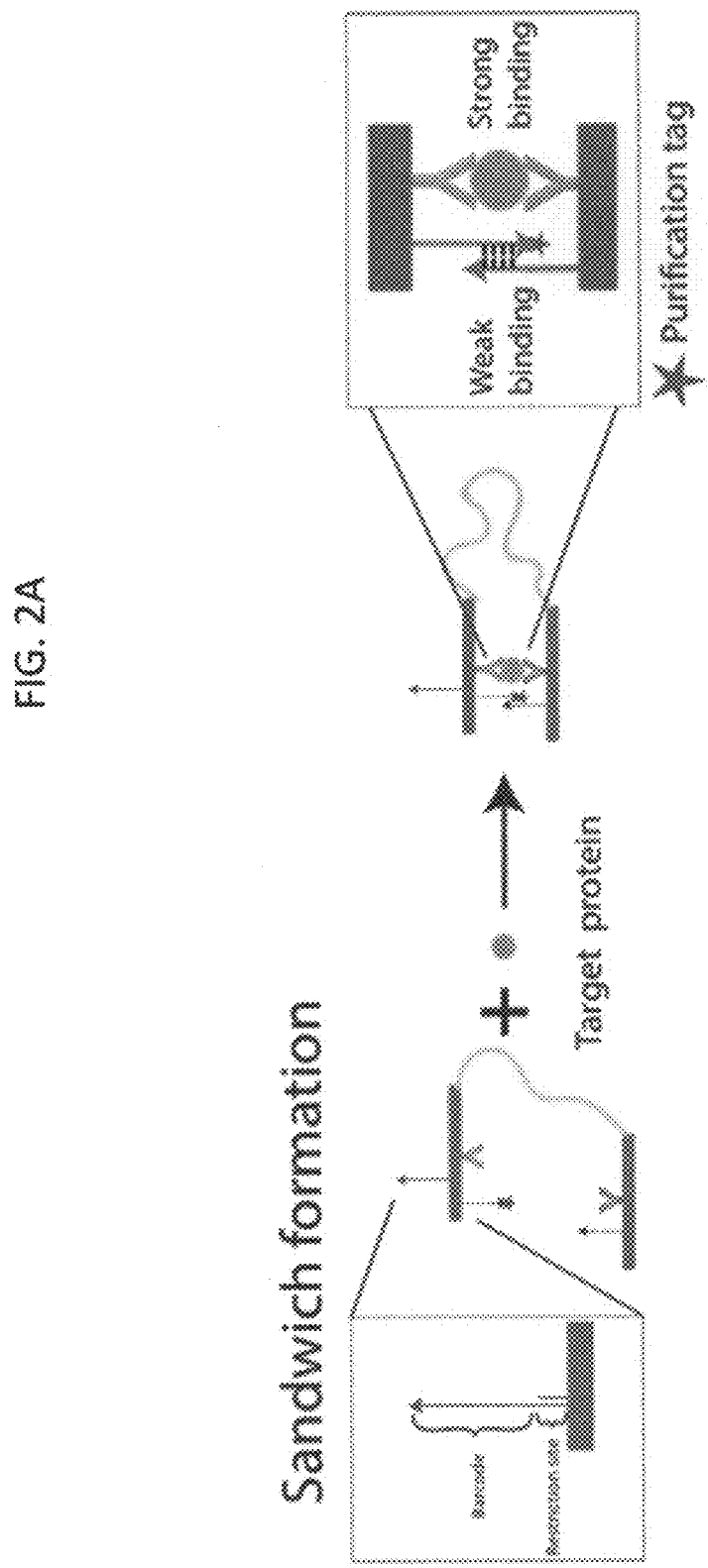
FIG. 2A is a schematic of the operation of a bistable sensor in solution, operating via a sandwich actuation mechanism, showing the hiding of an affinity tag upon binding of the analyte.
Figure 2B:
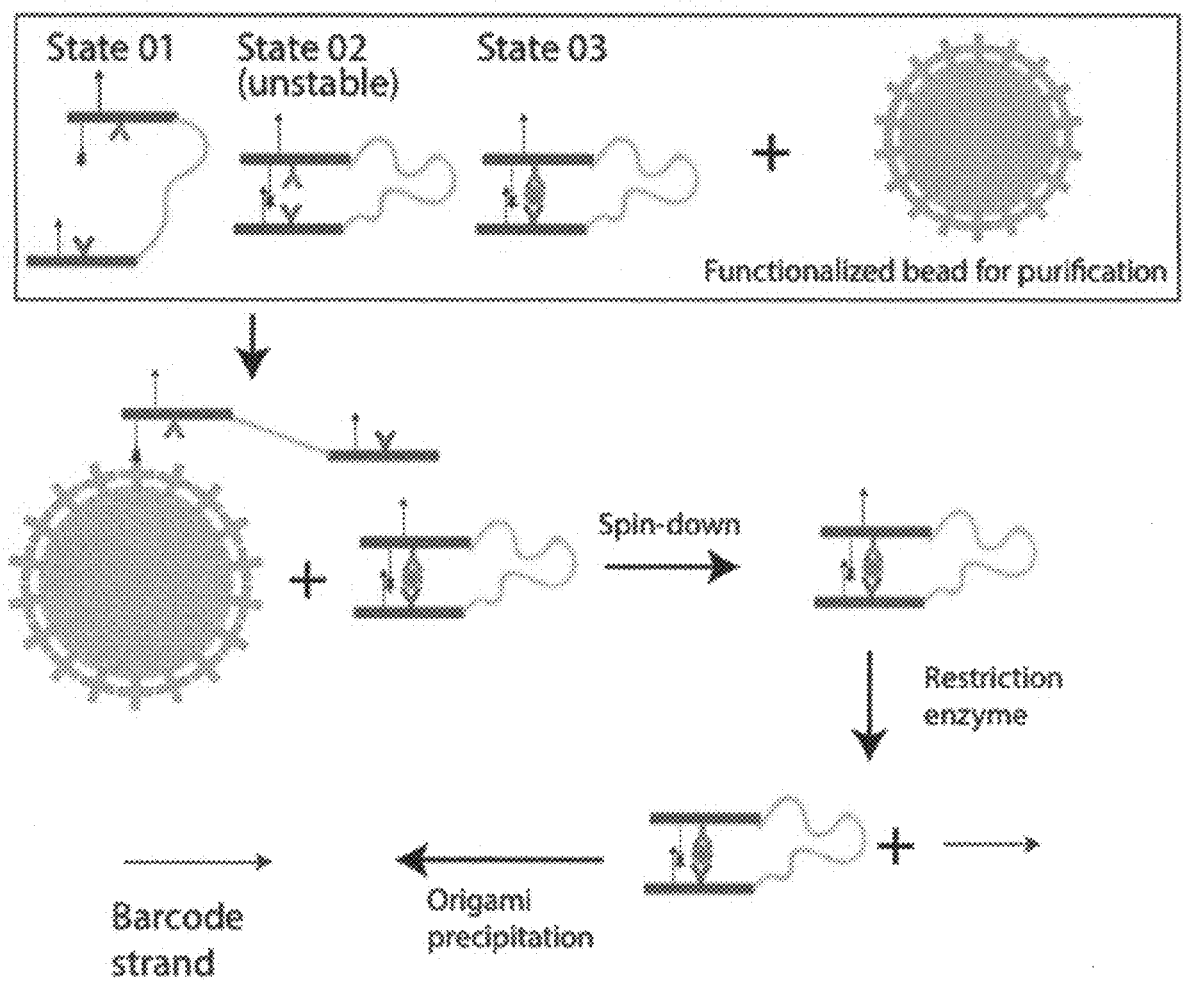
FIG. 2B is a schematic describing the extraction of the DNA barcode from bistable sensors which have closed, by removing open sensors using affinity beads.

For some "solution version" embodiments which provide detection via output of a DNA barcode signal, bistability of the devices allows us to preferentially remove devices which have not bound the target analyte (FIG. 2). Devices that are open have available purification tags (FIG. 2A, e.g. biotin), which can bind an affinity column (e.g. comprising streptavidin beads). The remaining closed devices, having bound analyte, have affinity tags which are hidden and so they should pass over the affinity column with beads that bind the affinity tag (FIG. 2B) and may be collected for analysis.

Once eluted from the affinity column, the closed, analyte-bound devices can be detected via standard PCR or quantified via quantitative PCR, droplet digital PCR, or various approaches to next-gen DNA sequencing or deep DNA sequencing, based on an attached DNA barcode. Depending on the exact approach used to detect and quantify the DNA barcode, the devices can be used without further treatment and purification, or the DNA barcode can be released from the bistable device and purified before being read out. In some embodiments the DNA barcode can be released from the bistable sensors through the use of a restriction enzyme, which cleaves the barcode molecule off of the sensor. In some embodiments the DNA barcode can be released from the bistable sensors via a strand displacement reaction as described in Zhang et al, "Dynamic DNA nanotechnology using strand-displacement reactions", Nature Chemistry 3 (2011): 103-113, the entire content of which is incorporate herein by reference. In some embodiments the DNA barcode is not released from the bistable sensor, and it is read directly.

Advantages of some solution-based embodiments which use a DNA barcode signal as output include: (1) they may be used with existing reagents (antibodies for a standard sandwich immunoassay can be coupled to the bistable device), (2) they may be used without instrumentation beyond that required for DNA amplification (e.g. PCR), (3) they enable a high degree of multiplexing, at least 8 analytes in the case of fluorescence-based qPCR and at least 1000 analytes in the case of next-generation sequencing and (4) they may be rendered highly quantitative by taking the DNA barcode output of a bistable sensor and using it as an input to droplet digital PCR (ddPCR). Thus a standard technique for counting of nucleic acids (ddPCR) can be used to count protein molecules via the use of bistable sensors.

The sensitivity, false negative and false positive rates of any particular solution based embodiment will be set by: (1) the binding affinity of the analyte for the binding molecules within the device, and the degree to which a bound analyte completely closes the device, (2) the degree to which the purification tags are 'hidden' in the bound state, and (3) the degree to which "unhidden" purification tags allow complete removal of devices which have not bound analyte from solution. For example, if the closed device still allows small molecule purification tags like biotin to project slightly from holes in the origami surface, then some analyte molecules may be lost on the affinity column, resulting in a false negative, or underestimate of protein concentration. Similarly, if the binding of an analyte to a bistable device is relatively weak, and the device is not persistently closed, and it still opens and closes dynamically, it may be lost on the column.

Accordingly, in some embodiments, additional 'weak locks', comprising a pair of short complementary single-stranded DNAs which activate when an analyte binds, may decrease false negatives. Weak locks will tend to shift the equilibrium of a device without analyte towards a closed configuration. If a such a device spends enough time in a closed configuration, specifically the average time that it takes for the device to pass over the column, then it may avoid binding the column, and create a false positive.

Accordingly, in embodiments which have weak locks, the strength of the weak locks must be tuned so that fluctuations (between open and near-closed) of a bistable device that has no analyte bound create enough opportunity for it to bind the affinity column, that it does so with high probability.

The more chances a device without an analyte bound has to bind to the column, the lower the chance that it will pass through and generate a false positive. Accordingly, in some embodiments multiple sequential affinity column separations may be used to decrease false positives.

With respect to the appearance of weak locks and affinity tags in FIG. 1A, the affinity tags have been drawn as being positioned at the termini of the single-stranded weak locks for purposes of clarity. Some embodiments have this configuration of weak locks and affinity tags. In other embodiments the weak locks and affinity tags are on separate linkers on the inside surfaces of the bistable sensor. In other embodiments there are no weak locks and the affinity tags are on linkers on the inside surfaces of the bistable sensor.

In the case of weak analyte binding, where a bistable device with a bound analyte often fluctuates into an open configuration (where the analyte is still bound to one of the two lids), the binding of additional copies of the analyte may serve to decrease the frequency of open configurations, if additional binding sites are available. Accordingly, in some embodiments of solution-based bistable sensors, the use of cooperativity, through the inclusion of multiple copies of each binding partner on the top and bottom lids of the sensor in a manner analogous to that shown for DNA detection on a surface in FIG. 4B (labelled "cooperative sandwich mechanism") may also decrease false negatives.

In some embodiments of solution-based bistable sensors, the use of a time-resolved optical output enables the use of bistable sensors in a widely installed base of commercial plate readers which are capable of measuring time-resolved luminescence of long-lived emitters. In such embodiments the solution-based sensor does not require a DNA barcode, or affinity tags or weak locks. Readout is based on Luminescence Resonance Energy Transfer between short-lifetime (nanosecond to microsecond) emitters (e.g. organic fluorophores or quantum dots) and long-lifetime emitters (millisecond) luminescent compounds such as europium and terbium chelates. In such embodiments, one lid of the bistable sensor is labelled with organic fluorophores. In some embodiments the organic fluorophores on one lid can be replaced by organic quenchers. In such embodiments a second lid of the bistable sensor is labelled with long-lifetime emitters such as europium and terbium chelates.

Depending on the specific wavelength used for the short-lifetime and long-lifetime emitters, energy transfer (from donor to acceptor) may be from the short-lived emitters to the long-lived emitters or vice versa. In either case, pulsed excitation light is used, and time-resolved measurements are made after the decay lifetime of the short-lived emitters has passed. In this way, all scattered excitation light has dissipated, the only signal measured is that which has transferred between short-lived and long-lived emitters, greatly increasing signal-to-noise and consequently sensitivity of the assay. The general principle behind such measurements, Luminescence Resonance Energy Transfer (LRET) has been previously described in Selvin et al, "Luminescence Resonance Energy Transfer" Journal of the American Chemical Society, 116(1994):6029-6030, the entire content of which is incorporate herein by reference.

If, on the other hand, the bistable sensor is immobilized on a surface (FIG. 1B) the binding of the analyte can be recognized as a state change measured electronically (FIG. 6) or optically (FIG. 7). Each embodiment of the surface-based approach to detecting the state change of the bistable device will have a different set of mechanisms for false positive and false negative errors than the solution approach, and so in some embodiments detection may be more quantitative than in others. For example, as discussed later for some embodiments, false positives may occur when the top origami shape nonspecifically binds to the surface (FIG. 9A), in the absence of analyte.

Like some solution embodiments, some surface-based embodiments achieve high sensitivity measurements. Some surface based-embodiments achieve high sensitivity through the use of TIRF microscopy (as described for single origami in Gietl et al "DNA origami as biocompatible surface to match single-molecule and ensemble experiments" Nucleic Acids Res. 40 (2012): e110 and Tsukanov et al, "Detailed study of DNA hairpin dynamics using single-molecule fluorescence assisted by DNA origami", Phys. Chem. B 117 (2013):11932-11942) or electrochemical detection (as described for reconfigurations of small nucleic acids in Lai, "Chapter Eight: Folding- and Dynamics-Based Electrochemical DNA Sensors", Methods in Enzymology, 589 (2017):221-252; Immoos et al, "DNA-PEG-DNA triblock macromolecules for reagentless DNA detection", Journal of the American Chemical Society 126 (2004):10814-10815; Wu et al, "Development of a "signal-on" electrochemical DNA sensor with an oligo-thymine spacer for point mutation detection", Chemical Communications, 49 (2013): 3422-3424; and Wu, et al, "Effects of DNA probe and target flexibility on the performance of a "signal-on" electrochemical DNA sensor" Analytical Chemistry 86 (2014) 8888-8895) the entire contents of all of which are herein incorporated by reference, wherein binding of an analyte nucleic acid to a nucleic acid on a surface brings an electrochemically active functional group (ferrocene or methylene blue) proximal to a surface where it can be electronically detected.

In some embodiments, surface-based optical and electronic measurements can be converted from analog measurements to digital measurements through the use of DNA origami positioning technologies. Digital measurement can be achieved using DNA origami because individual DNA origami can be almost deterministically (>95% of sites have a single origami) spaced out into a grid on a surface using lithographic techniques for positioning them as described in Kershner et al, "Placement and orientation of individual DNA shapes on lithographically patterned surfaces", Nature Nanotechnology 4 (2009):557-561; Hung et al, "Large-area spatially ordered arrays of gold nanoparticles directed by lithographically confined DNA origami", Nature Nanotechnology 5 (2010): 121-126; Gopinath et al, "Optimized Assembly and Covalent Coupling of Single-Molecule DNA Origami Nanoarrays", ACS Nano 8 (2014):12030-12040; and Gopinath et al, "Engineering and mapping nanocavity emission via precision placement of DNA origami", Nature 535 (2016): 401-405, the entire contents of all of which are herein incorporated by reference. Such previously described "DNA origami placement" techniques enable individual bistable sensors to be positioned on individual optical or electronic devices with a probability of >95%, and thus >95% of sensors will be available for sensing target molecules. This stands in contrast to droplet digital PCR which relies on Poisson statistics to populate drops with individual analyte nucleic acids, achieving a single nucleic acid in no more than 37% of drops. Thus some embodiments of the surface-based approach to reading out bistable sensors may give more quantitative results than some solution-based methods which rely on droplet digital PCR for readout.

Figure 10:
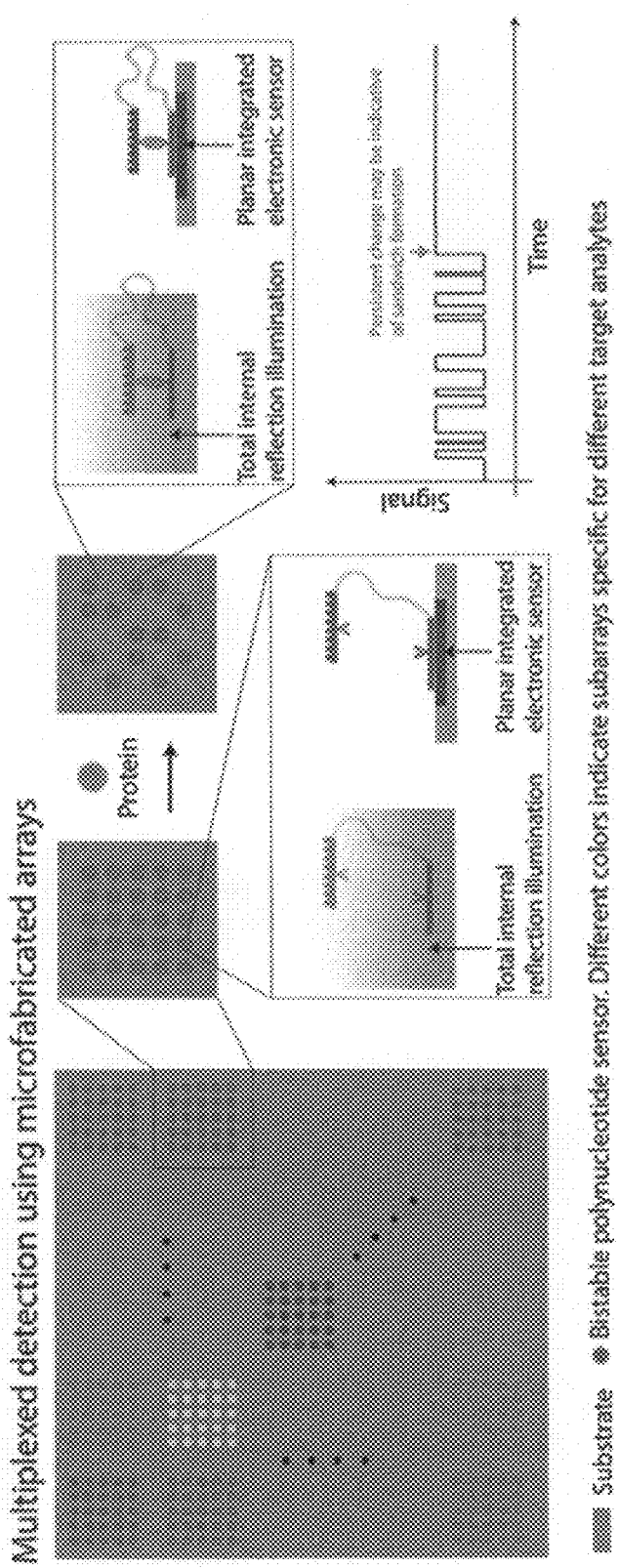
FIG. 10 depicts the multiplexed detection of multiple analytes via the use of multiple arrays of bistable sensors, where each sub-array is sensitive to a distinct analyte of interest.

Some surface-based embodiments achieve a high degree of multiplexing by using widely available technology to print spots of surface-immobilized devices with specificity to a different analyte. FIG. 10 shows that each spot will have thousands of devices with the same pair of binding molecules, but different spots will have different pairs of binding molecules. Some embodiments accomplish this spatial multiplexing with ink-jet printing and other embodiments achieve multiplexing with microarray spotting.

Similar to some solution-based embodiments, some surface-based embodiments may use existing sandwich ELISA reagents for binding target molecules, but such embodiments may require additional materials (electronic or optical chips) and instrumentation (an electronic reader or TIRF/other optical reader or microscope).

Some embodiments of the present invention exhibit the first instance of an assay having one or more of the following properties: (1) A bistable DNA nanostructure device to convert analyte binding signal into a unique and amplifiable DNA signal, based on the principle of hiding a purification tag (changing the state of the device from open to closed). (2) An assay with multiple surface-based methods for sensitively measuring the conversion of a large and flexible bistable DNA device into a small, compact, rigid device upon binding of a single analyte molecule. (3) An assay with the ability to multiplex the quantitative measurement of multiple analytes based on the bistable DNA nanostructure device described, either in solution via PCR/sequencing or on a surface via the spatial location of an optical or electronic signal. (4) An assay which can provide digital quantification of protein molecules, at the same scale as digital droplet PCR.

Some embodiments of the present invention provide significant improvements over existing electrochemical assays. Folding-based assays as described (Lai, "Chapter Eight: Folding- and Dynamics-Based Electrochemical DNA Sensors", Methods in Enzymology, 589 (2017):221-252; Immoos et al, "DNA-PEG-DNA triblock macromolecules for reagentless DNA detection", Journal of the American Chemical Society 126 (2004):10814-10815; Wu et al, "Development of a "signal-on" electrochemical DNA sensor with an oligo-thymine spacer for point mutation detection", Chemical Communications, 49 (2013): 3422-3424; and Wu, et al, "Effects of DNA probe and target flexibility on the performance of a "signal-on" electrochemical DNA sensor" Analytical Chemistry 86 (2014) 8888-8895) have been used to detect conformational changes due to the binding of a nucleic acid to a detector on a surface via electrochemical sensing (using ferrocene or methylene blue signaling molecules). In this setting a single nucleic acid brings a single signal molecule close to the surface when an analyte nucleic acid binds and folds the overall structure so that the signaling molecule is close to the surface.

Embodiments of the present disclosure differ in important ways: (i) The disclosed work enables protein or arbitrary analytes to be examined where previous work is limited to DNA or RNA. (ii) Previous work uses a single signal molecule per binding event. The presently disclosed use of DNA origami or another large DNA nanostructure means that the presently disclosed signal may be much stronger; at least 200 signal molecules may be incorporated on one of the origami, providing amplification so that the present assay is in principle 200 times more sensitive. (iii) Previous work folds the detecting molecule just a few nanometers. This means that the signal molecules do not move very far from the inactive (no analyte) to active (analyte bound) state. In turn this means that the inactive and active states are not as strongly differentiated as they could be, and the assay is not as potentially sensitive as it could be. In the presently disclosed work, the tether could be up to several microns long (tunable all the way down to a few nanometers). This will allow the origami carrying the signaling molecules to be positioned at an optimal height above the surface to minimize the signal in the inactive state, thereby maximizing the sensitivity to the analyte bound state. In previous work, short linkers limited the detection method to electrochemical sensing. In the presently disclosed work, because the linker can be long enough (e.g. 200 nanometers) to move the signaling molecules significantly out of the evanescent field of a TIRF substrate in the inactive state, TIRF microscopy will be able to achieve much higher sensitivity.

Embodiments of the present invention provide significant improvements over existing TIRF-based assays. TIRF has been used on surface-bound origami for the detection of molecular binding or conformational changes previously (Gietl et al "DNA origami as biocompatible surface to match single-molecule and ensemble experiments" Nucleic Acids Res. 40 (2012): e110 and Tsukanov et al, "Detailed study of DNA hairpin dynamics using single-molecule fluorescence assisted by DNA origami", Phys. Chem. B 117 (2013): 11932-11942). These studies provide support that the presently disclosed method can be used for quantification of proteins in a low volume/low concentration/single-molecule regimes. However, these previous studies: (i) Studied nucleic acids rather than proteins, and give no facility for using two binding molecules to simultaneously engage an analyte (as in a sandwich assay). (i) Studied conformational changes of very simple hairpin or Holliday junctions using single signaling molecules. The presently disclosed much larger devices will have more than 200 signaling molecules for greater amplification and sensitivity of molecular events. (ii) Used short linkers/small conformational changes. Again the presently disclosed work uses a very large conformational change which will enable a higher sensitivity for the same number of signaling molecules.

Bistable origami detectors have several advantages over other potential methods. In the language of immunoassays (which also applies to DNA and RNA detection, but is not generally used for nucleic acid detection) bistable detectors can serve as the basis of "homogeneous assays", in which a sample to be analyzed can be simply added to the detector, without any requirement for components of the detection system to be mixed together, and importantly without the requirement that extra sample be washed away, or that a secondary detection system be added. This means that a detection experiment can proceed directly and quickly. Secondly, because origami domains are typically very large (several megadaltons) they are typically 100-1000× times larger than the molecules being detected (kilodaltons to tens of kilodaltons). This means that origami can carry numerous signaling molecules, which can give a 200-fold amplification without the use of a secondary amplification system.

Figure 3A:
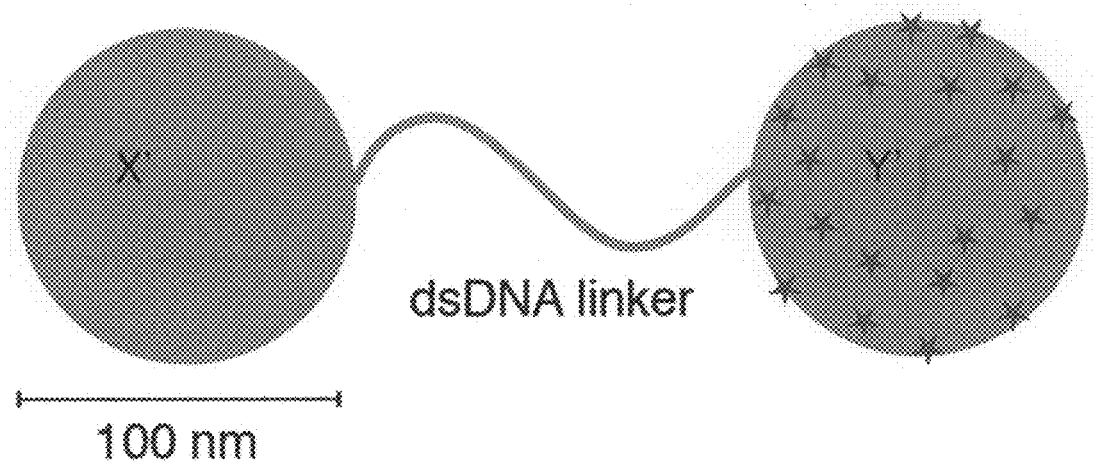
FIGS. 3A-C depicts a bistable sensor suitable for sensing single-stranded nucleic acids using a sandwich actuation, adapted for optical or electronic detection on a surface.
Figure 3B:
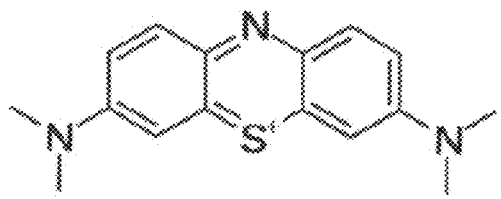

In FIG. 1 and FIG. 2, embodiments employing a sandwich actuation mechanism using antibodies for the detection of proteins are depicted. FIG. 3 depicts different embodiments that employ a sandwich actuation for the detection of nucleic acids. FIG. 3A shows the basic geometry of a flytrap device on a surface. It includes two 100 nanometer diameter DNA origami disks or "lids", and a 10 nanometer to 4,000 nanometer double-stranded DNA linker between them. Detection of a single-stranded target nucleic acid sequence XY is mediated by a pair of probes X' and Y' which are each complementary to one-half of the target sequence and are bound to the inside of the top and bottom lids, respectively.

In the absence of XY, the lids of the flytrap will diffuse independently, restricted by the tether, in what is referred to in this disclosure as the "open" state. When both domains X and Y bind to their complementary probes on the flytrap, in what is referred to in this disclosure as the "closed" state, the two lids of the device will be co-localized, with a distance set by the particular probe-target/device geometry chosen. For example, if probes are chosen so that they are tethered to the lid at a position which is at the end of the probe-target duplex, then lids will be held at a distance roughly equal to twice the length of a single probe-target duplex (~7 nm for a pair of 10-mer probes, ~14 nm for a pair of 20-mer probes). If on the other hand probes are chosen so that they are tethered to the lids in a geometry that puts the linker adjacent to the middle of the probe-target duplex, then the lids can be held at a distance of roughly 2-4 nanometers (at most the width of two DNA helices) independent of the length of the target sequence.

Figure 3C:
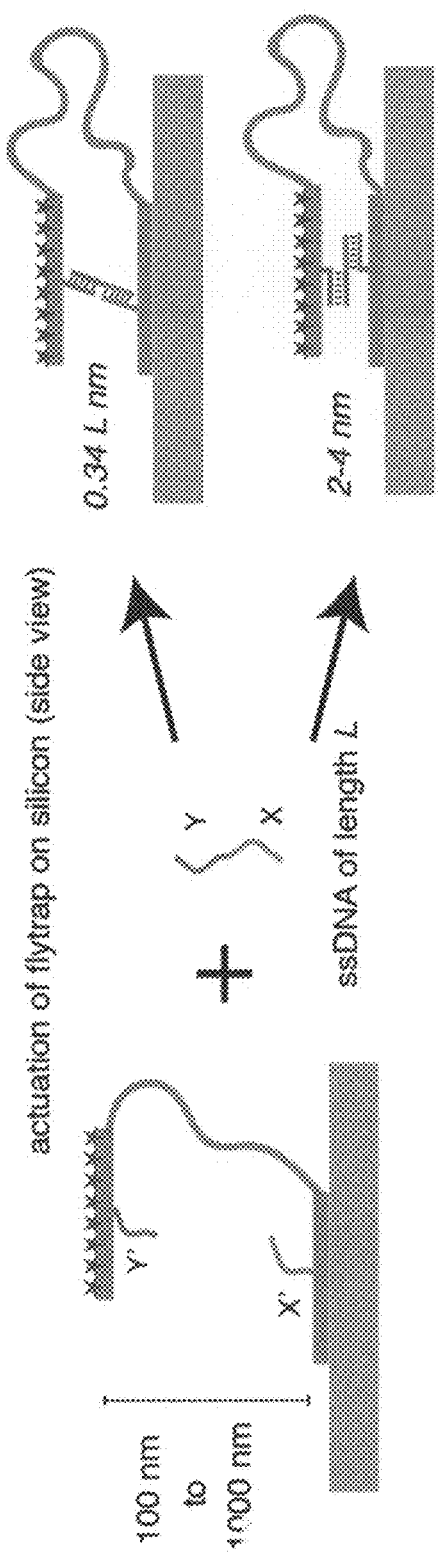
Figure 3D:
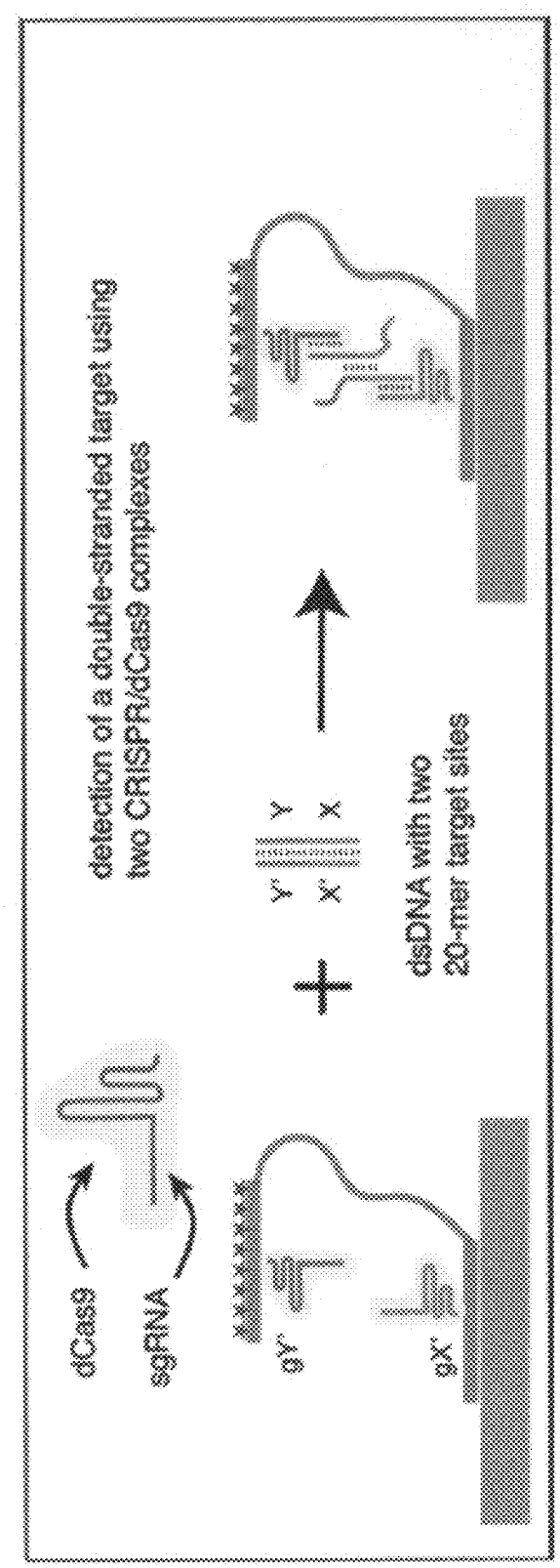
FIG. 3D depicts a bistable sensor suitable for sensing double-stranded DNA, using sandwich actuation, using two CRISPR/dCas9 complexes.

The flytraps described in FIG. 3C will be most efficient for detecting a single-stranded DNA, single-stranded RNA, or other single-stranded polynucleotide analogs. For special DNA duplex sequences, namely those capable of forming DNA triple helices, the flytraps in FIG. 3C may be used to detect double-stranded DNA, although the kinetics of DNA triple helix formation are slow, and target analytes would be constrained to polypurine:polypyrimidine triplex-forming sequences.

On the other hand, through the use of dCas9/CRISPR complexes, it is possible to create flytraps capable of efficiently detecting double-stranded DNA via two different methods. In the CRISPR system, dCas9 proteins complex with gRNAs, each of which has a 20-nucleotide RNA "guide" sequence. With the aid of the dCas9, the guide sequence can strand-displace into an appropriate double-stranded DNA and essentially irreversibly bind a complementary target.

Accordingly, in some embodiments (FIG. 3D) each lid has an attached gRNA having one of two different guide sequences, chosen to so that they bind adjacent pairs of 20-nucleotide targets in a DNA sequence of interest. Before introduction of the analyte DNA, dCas9 protein is introduced and assembled onto the gRNAs. Consequently, simultaneous binding of two CRISPR/dCas9 complexes to a single double-stranded analyte DNA will close the flytrap.

In such an embodiment, a caveat is that target sequences must be adjacent to so-called PAM-sites having a particular consensus sequence, for example NGG. Thus in the case of natural DNAs, detection with conventional dCas9 will be limited to DNA sequences which coincidentally have two appropriately-spaced PAM-sites (within about 50 nucleotides). Recently analyzed GFP constructs were used as controls in CRISPR-based gene regulation experiments and several stretches of DNA were found to have double-occurrences of PAM sites at distances appropriate for the dual-target detection scheme depicted in FIG. 3D. Further, in some embodiments, Cas proteins (or any suitable endonuclease) from organisms other than *S. Pyogenes*, and engineered endonuclease proteins (e.g., Cas9) with different sequence specificity for their PAM sites will enable a greater range of sequences to be detected. In the case where the target analyte is an artificial DNAs used in bar-coding schemes or in DNA storage, the addition of pairs of PAM sites wherever necessary presents no difficulty.

The advantage of embodiments with such dual-target schemes is that they will work with standard gRNA sequences. Further, atomic force microscopy (AFM) data (FIG. 3F), shows that dCas9 with artificial guide sequences readily binds short artificial targets along the edge of an origami. Thus CRISPR/dCas9 complexes integrate well with DNA origami at desired locations. The dual-target scheme requires that the DNA-binding part of CRISPR/dCas9 be free, rather than bound to origami, as in FIG. 3F. Accordingly, in some embodiments, 3' extensions of the gRNAs will be used to secure a CRISPR/dCas9 complexes to the flytrap.

The limiting sequence constraint of such dual target schemes is that they require DNA analytes to have two target/PAM sites, and a length of at least 46 nucleotides. Other embodiments enable the detection of double-stranded DNA with fewer sequence constraints. Dynamic DNA and RNA nanotechnology makes use of nonequilibrium DNA reactions to create cascades of ordered events (as described in Zhang et al, "Dynamic DNA nanotechnology using strand-displacement reactions", Nature Chemistry 3 (2011): 103-113). A classic example is the so-called hairpin-chain reaction. Reactions of this type enable a sequence to remain "hidden" via another protecting sequence which forms a hairpin, until a trigger sequences binds.

Figure 3E:
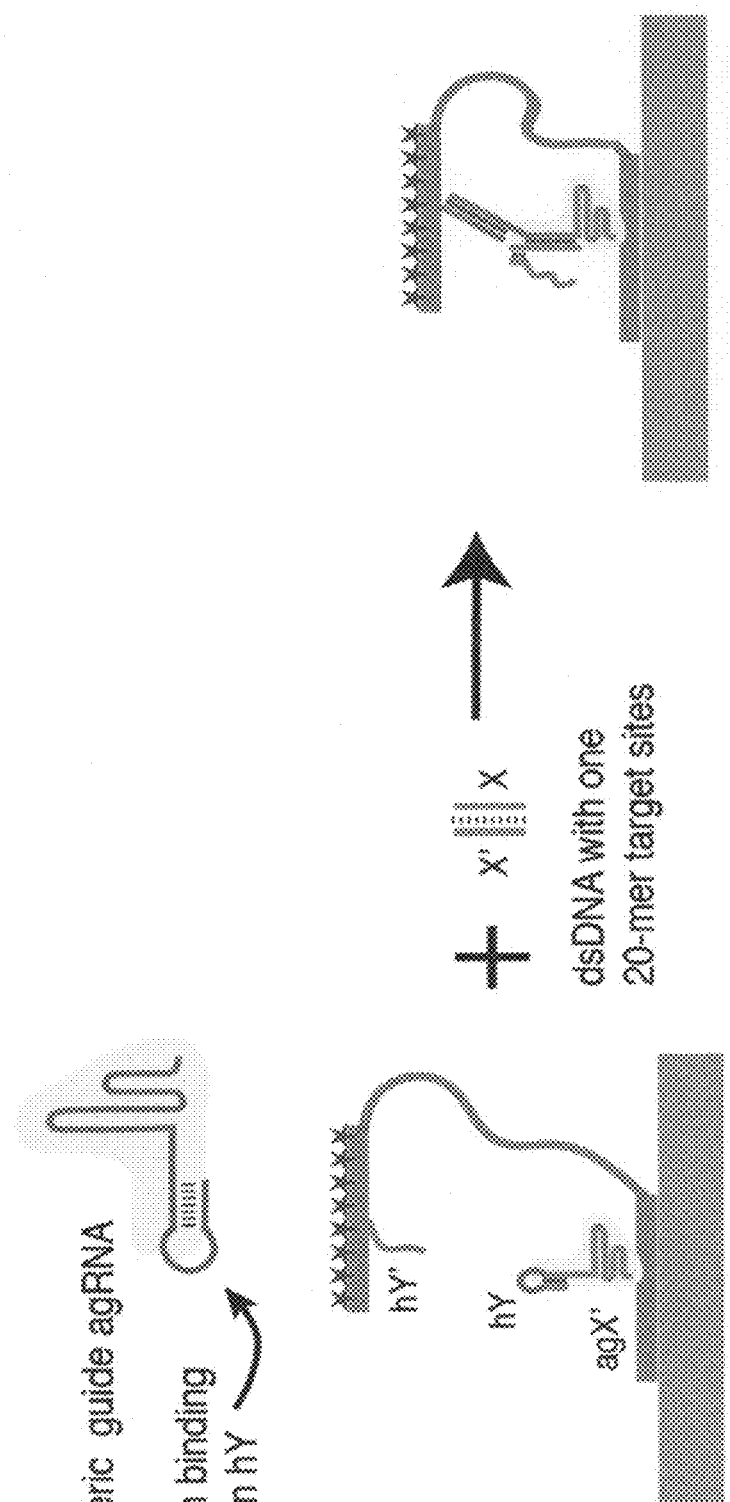
FIG. 3E depicts a bistable sensor suitable for sensing double-stranded DNA using sandwich actuation, using a single allosteric CRISPR/dCas9 complex, which reveals a hidden sequence upon binding a double-stranded analyte.
Figure 3F:
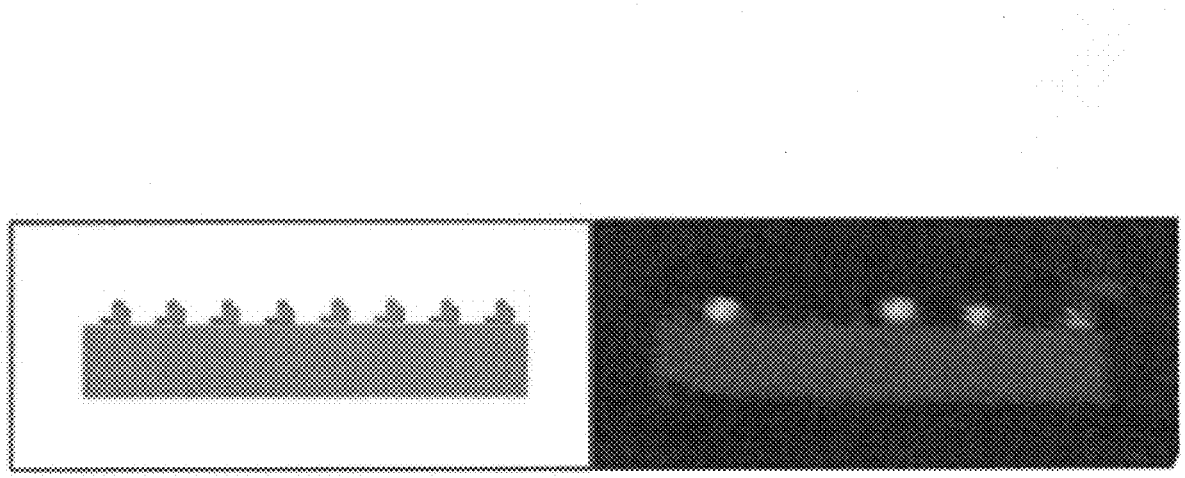
FIG. 3F shows a schematic (left) and an image (right) of atomic force microscopy (AFM) data of dCas9 with artificial guide sequences readily binds short artificial targets along the edge of an origami, according to embodiments of the present disclosure.

Accordingly, the principle of hiding a sequence to create a so-called "allosteric" CRISPR/Cas9 complex can be used to achieve a double-stranded DNA sensor (FIG. 3E). Positioned on the bottom lid of the fly trap, an allosteric CRISPR/Cas9 will, upon binding to its target double-stranded sequence X, reveal a new sequence hY complementary to a sequence hY' on the lid of the flytrap, causing the flytrap to close. To do this the 5' end of the gRNA may be extended with a new sequence that will form a hairpin with the guide sequence. Thus the guide sequence serves to hide and protect the sequence hY from hY' until a double-stranded DNA (X) of interest binds the allosteric CRISPR/Cas9.

Here the use of the term allosteric is a consistent with the standard use of allosteric in the literature, yet is somewhat unusual. By definition allostery simply involves the ability of one molecule, an effector A, to change the binding or activity of a second molecule B (typically a protein) towards a third molecule C. In the allosteric scheme given here, the double-stranded DNA of interest plays the role of the effector A, the CRISPR/dCas9 complex plays the role of B, and the sequence on the lid of flytrap plays the role of C. The scheme in FIG. 3E is unusual in that allostery is usually defined over the "normal" activity of a protein. Here the "normal" activity of the protein is used as the allosteric trigger to switch on or off a new function for the protein—that of binding the flytrap lid. This kind of scheme is not thought to have been reported in the literature of CRISPR/cas9, although standard allostery, in which a small molecule (4-hydroxytamoxifen) switches the activity of CRISPR/cas9, has been described (Oakes et al "Profiling of engineering hotspots identifies an allosteric CRISPR-Cas9 switch", Nature Biotechnology 34 (2016):646-651).

The advantage of the allosteric scheme in FIG. 3E for detection double-stranded DNA is that it requires only a single 20-nucleotide target plus its 3-nucleotide PAM site. It is noted that XRN-1 5'-to-3' exonuclease or other activities have appeared to inhibit the useful addition of functional sequences to the 5' end of gRNAs in vivo in yeast and mammalian cells (such additions are unprotected by the protein envelope of Cas9). Here, because in vitro DNA detection is being performed, such extensions will not be degraded. In some embodiments, small (<10 nt stem) hairpins may be used to avoid interfering with the initiation of the CRISPR/Cas9 DNA complex at the important first 10 nucleotides of the guide (close to the PAM site), and to maximize the sensitivity of the sensor.

Some natural sequences of interest will inevitably be missing NGG, but in these cases, the use of different natural or mutant CRISPR systems with different PAM sites (such as the Cas-protein Cpf1 from *Prevotella* and *Francisella* bacteria, with its TTTN PAM site) will greatly increase the chances of finding a usable target sequence in some embodiments. Further, Cpf1 has a totally different gRNA structure and a 3'-end guide sequence than does dCas9, which may prove more compatible for some target sequences. Accordingly, in some embodiments, CRISPR/Cpf1 will be used in place of CRISPR/dCas9.

Figure 4A:
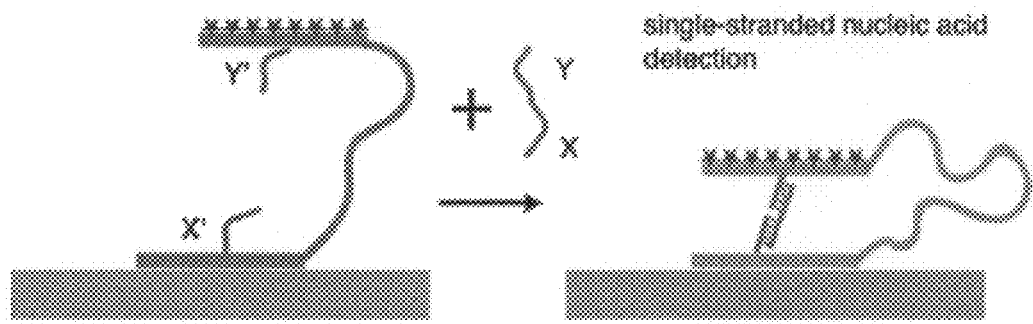
FIGS. 4A-F depict the three major mechanisms of actuation, sandwich, competitive, and functional, including examples of these mechanisms which use cooperativity, detect the phosphorylation of MAPK, or the binding of a ligand to a transmembrane G-protein coupled receptor.
Figure 4B:
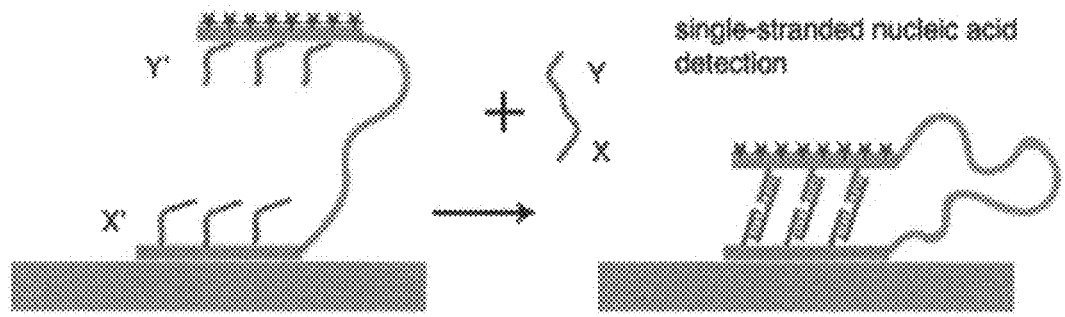
Figure 4C:
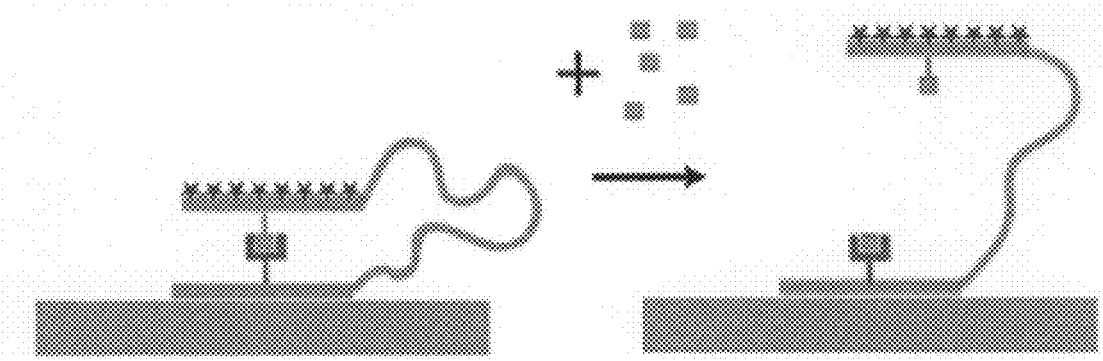
Figure 4D:
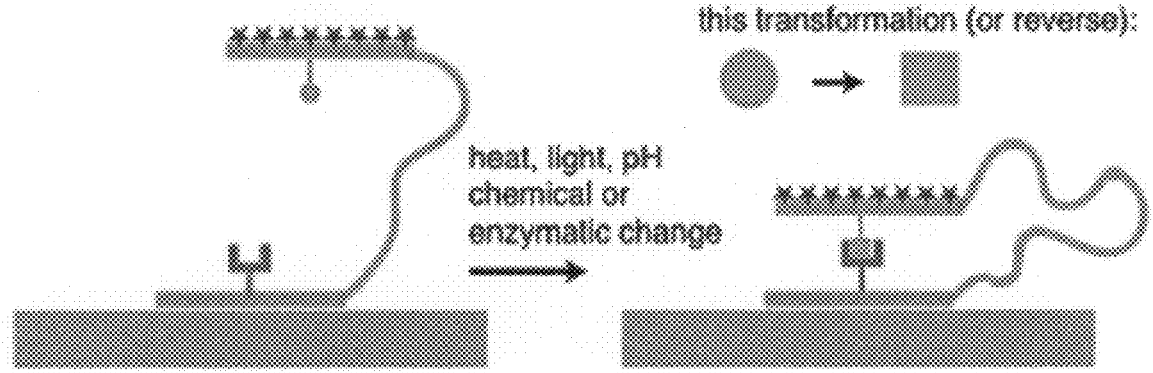
Figure 4E:
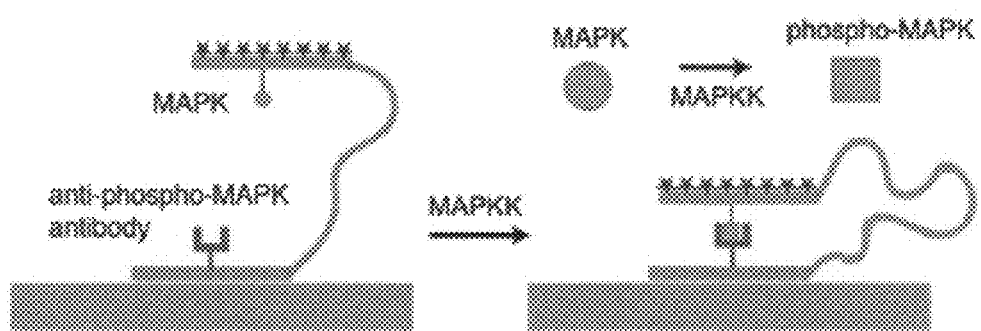
Figure 4F:
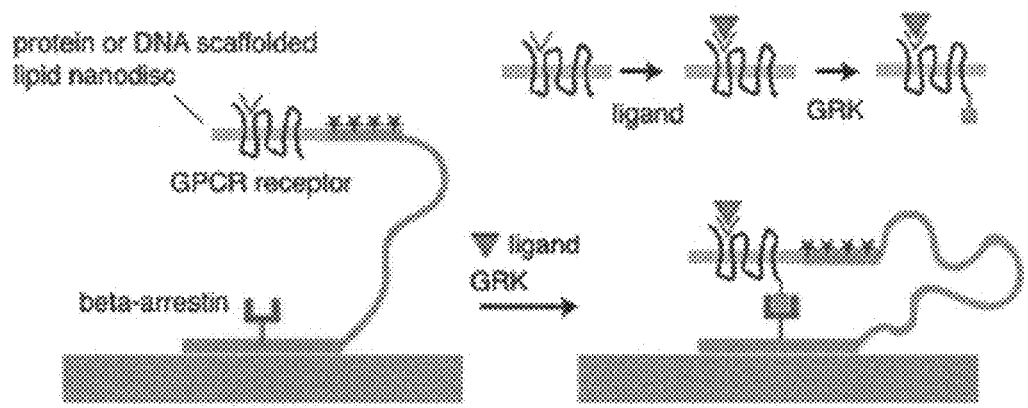

In FIGS. 1-3, embodiments are depicted which use a sandwich actuation mechanism for detecting and quantifying molecular binding events, towards the quantification of analytes such as protein and nucleic acids were described. FIG. 4 and FIG. 5 describe bistable molecular sensors in additional contexts. The basic bistable sensor design has several "actuation mechanisms" in which the role of the top lid and the bottom lid of the sensor have different roles relative to the detection of a molecule event, and these roles differ based on whether the molecular event is a binding event, conformational change or other molecular event. As shown in FIGS. 4A, 4C, and 4D, it is distinguished whether the sensing mechanism is a "sandwich mechanism" (FIG. 4A, for binding events), a "competitive mechanism" (FIG. 4C, for binding events), or a "functional mechanism" (FIG. 4D, for conformational changes whether induced by a molecule or physical environment, enzymatic or chemical cleavage, or enzymatic or chemical modification). Additionally, a sensor described as operating in a sandwich, competitive, or functional mechanism can further be described as operating either in either a non-cooperative or a cooperative mechanism (e.g. FIG. 4B).

The sandwich actuation mechanism (FIG. 4A) has been described over a "sandwich" design in which a pair of binding partners (antibodies, RNA or DNA aptamers, natural binding protein, etc.) for a target analyte are positioned on the top and bottom lid of the sensor, respectively. The sandwich mechanism is good for detecting the presence or absence of an analyte or measuring concentrations. In the case that antibodies are used as binding partners, the sandwich assay is comparable to a sandwich immunoassay, for example a sandwich ELISA.

For a particular molecular analyte of interest, a sandwich mechanism (FIG. 4A) is appropriate for its detection if an appropriate pair of binding partners can be found. This is typically the case for larger target analytes, such as proteins, for which two different epitopes can be found, with one binding partner having affinity for each epitope. For cases where the target analyte is single-stranded DNA or single-stranded RNA, the two binding partners can be single-stranded, where each binding partner is itself a single strand of DNA or RNA, complementary to a different region or subsequence of the target analyte. In the case where the target analyte is a double strand of DNA, RNA:DNA hybrid, or double-stranded RNA, the binding partners could be (1) single-stranded DNA or RNA (in which case the sensors would close upon formation of a triplex) at two different regions or subsequences of the target analyte, or (2) the binding partners could be nucleic acid/protein complexes (such as CRISPR/dCas9) capable of sequence-specifically binding the target at two locations (as diagrammed in FIG. 3D), (3) the binding partner could be an allosteric CRISPR/dCas9 complex (as in FIG. 3E) or (3) the binding partners could be zinc-finger proteins, or peptides molecules capable of sequence-specifically binding the target at two regions or subsequences, or (4) any pair of molecules capable of sequence-specifically binding the target at two different regions.

The competitive actuation mechanism (FIG. 4C) is described for the situation in which the bottom lid of the sensor holds a single binding partner (antibody, RNA or DNA aptamer, natural binding protein, etc.) for a target analyte, and the top lid of the sensor holds a competitor molecule, which can bind the binding partner on the bottom lid in a manner that is similar to the target analyte. The competitive mechanism is good for detecting the presence or absence of an analyte or measuring concentrations. In the case that the binding partner is an antibody, the competitive mechanism is analogous to a competitive immunoassay. The competitive mechanism is useful in instances where the target analyte is too small or has a surface that is too symmetric or too chemically undifferentiated for two different binding partners for the target to be found. This will often be the case for small molecules such as typical drugs or many hormones. The fact that the competitive actuation mechanism requires only a single antibody or single aptamer for a particular target analyte makes the number of potential analytes available to the competitive actuation mechanism vastly larger than the number of potential analytes available to the sandwich actuation mechanism, which requires that two antibodies or two aptamers for a target of interest be found.

In the competitive actuation mechanism, the role of the top and bottom lids may be interchanged, depending on the potential for the binding and the competitor to nonspecifically bind the substrate surface adjacent to the sensor (which would typically cause a false negative signal); the molecule with the lower nonspecific affinity for the background surface typically being chosen to be positioned on the lid.

The competitor molecule can be an instance of the target molecule, a related molecule to the target molecule which can bind the binding partner, or any other molecule which can bind the binding partner at the site which the target would normally bind. This is so that the competitor, upon binding the binding partner, blocks or otherwise inhibiting the normal binding of the target. Similarly, the target analyte has the capability of binding the binding partner and inhibiting binding of the competitor. In the absence of target, the competitor binds the binding partner often, and the top lid of the sensor spends more time close to the bottom lid and the surface, producing a signal. In the presence target, the target molecule binds the binding partner on the bottom lid of some sensors, and decreases the amount of time the competitor is bound to the binding partner, and thus changing the signal. As the target concentration increases, the target has a higher occupancy on the binding partner, and the sensor is more often open, and the top lid spends more time away from the surface, enhancing the signal change.

The fact that presence of an analyte increases the probability of an open state does not imply that all embodiments of the competitive actuation mechanism must be "signal-off" detectors. Accordingly, the signal change in the competitive actuation mechanism may be positive or negative, depending on the particular sensing modality used to create and measure signal. The competitive assay may, for example, be used with an optical sensing modality in which the lid is labelled with a first fluorophore. In the situation that the bottom lid is labelled with a second fluorescent acceptor, then addition of the target would result in decrease of FRET between the first fluorophore and the second fluorophore, decreasing signal from the second fluorophore, thus implementing a "signal-off" detector. In the situation that the bottom lid is labeled with a fluorescent quencher, then addition of a target would decrease quenching between the first fluorophore and the quencher thus implementing a "signal-on" detector. Thus, as for other actuation mechanisms, the competitive mechanism can result in both signal on and signal off sensors, as desired.

The functional actuation mechanism (FIG. 4D) enables more general detection of molecular events, including binding of a class of molecules rather than a single target analyte, enzymatic or chemical activity including cleavage or ligation, or enzymatic or chemical modification for example phosphorylation, methylation or acetylation. In the functional mechanism, the top lid and bottom lid each carries a functional partner, (functional partner 1 and functional partner 2, respectively), which either bind each other or release in the presence of an external stimulus, which could be a small molecule or protein enzyme, but which could be a physical condition such as change in temperature, light, pH, or ionic strength.

In general, the roles of the top and the bottom lids can be interchanged, that is functional partner 1 could be on the top lid and the functional partner 2 could be on the bottom lid, or vice versa. Accordingly, the choice of which functional partner goes on the top lid typically depends on which functional partner has the lowest nonspecific binding to the background substrate. However, in some embodiments such as when one of the functional partners is a transmembrane protein, performance of the sensor may be increased when the transmembrane protein is attached to the top lid, and the other functional partner is attached to the bottom lid. In many embodiments, the external stimulus will cause a conformational change in functional partner 1 which will change its affinity for functional partner 2. In such embodiments, functional partner 2 is an antibody which is raised against functional partner 1 so that it binds functional partner 1 in a particular conformational state, but not another conformational state. In many embodiments, the external stimulus will cause a chemical modification of functional partner 1 (e.g. phosphorylation) which will change its affinity for functional partner 2. In such embodiments, functional partner 2 is an antibody which is raised against functional partner 1 so that it binds functional partner 1 in a particular state of modification (e.g. phosphorylated), but not another conformational state (e.g. unphosphorylated).

Accordingly, in one embodiment of the functional actuation mechanism (FIG. 4E) enables the detection of the phosphorylation of by mitogen-activated protein kinases (MAPK, e.g. P42 or P44) by mitogen-activated protein kinase kinase (MAPKK), or any other agent which phosphorylates MAPK. In this embodiment the functional partner 1 is MAPK (on the bottom lid), and functional partner 2 is an antibody which binds only to the phosphorylated form of MAPK (anti-phospho-MAPK). When the MAPK is unphosphorylated the sensor is open, when it is phosphorylated, the sensor is closed. Analogous embodiments can be constructed by replacing functional partner 1 with any protein that can be modified (via methylation, phosphorylation, or acetylation) and replacing functional partner 2 with a binding partner that only binds the modified version of partner 1.

Accordingly, in one embodiment of the functional actuation mechanism enables the detection of ligands, agonists or antagonists for a protein receptor such as any G-protein coupled receptor (GPCR). In this embodiment (FIG. 4F), functional partner 1 is either a protein-based lipid nanodisc (as described in Bayburt et al, "Membrane Protein Assembly into Nanodiscs" FEBS Letters 584 (2010):1721-1727), or a DNA-based lipid nanodisc as described in Zhao et al, "DNA-Corralled Nanodiscs for the Structural and Functional Characterization of Membrane Proteins and Viral Entry, Journal of the American Chemical Society, 140 (2018): 10639-10643 and Iric et al "DNA-Encircled Lipid Bilayers" Nanoscale (2018) DOI:10.1039/C8NR06505E), with a transmembrane receptor protein such as the mu-opiod receptor (a prototypical GPCR) loaded into the lipid part of the nanodisc, the entire contents of all of which are herein incorporated by reference. Protein-based lipid nanodiscs for the purpose of solubilizing membrane proteins are well-studied, and they can be linked to DNA strands as is taught in [cite Shih], thus providing a method to attach functional partner 1 to the top lid. Similarly, DNA-based lipid nanodiscs as disclosed in Zhao et al. and Iric et al., supra, may be loaded with membrane proteins, and can be attached to the top lid of the sensor, or can serve directly as the top lid of the sensor. The functional partner 2 is a protein, such as B-arrestin, whose affinity for the transmembrane protein changes when the receptor protein binds a ligand. In the particular case of using beta-arrestin as functional partner 2, ligand binding and activation of the GPCR in the top lid will cause a G protein—coupled receptor kinases (GRK) present in solution to phosphorylate the GPCR, which will cause the beta-arrestin to bind the GPCR and close the sensor. This embodiment provides a general method for the screening of drugs for GPCR in an in vitro cell free setting. In this setting, the sensor does not simply bind and sense a particular target analyte, but rather responds to any molecule which affects the normal biological function of the receptor being studied. In this case, a functional sensor is said to be a "class detector".

Figure 5A:
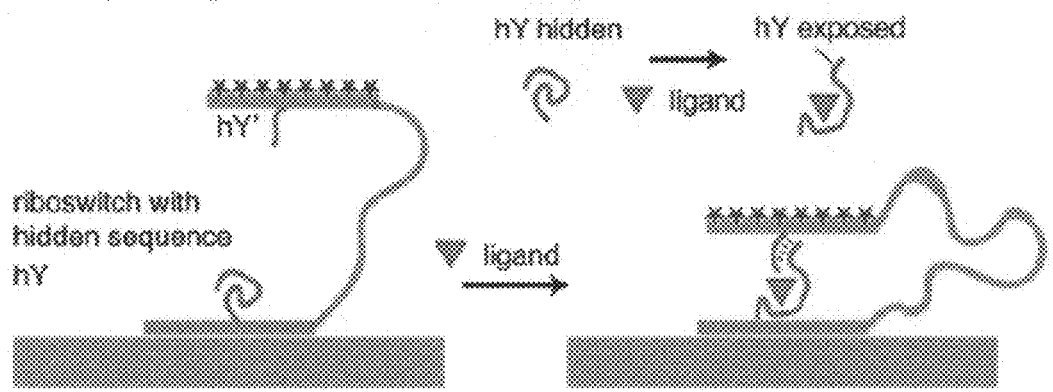
FIGS. 5A-D depict functional actuation of a bistable sensor based on a riboswitch, cleavage reactions, and ligation reactions.
Figure 5B:
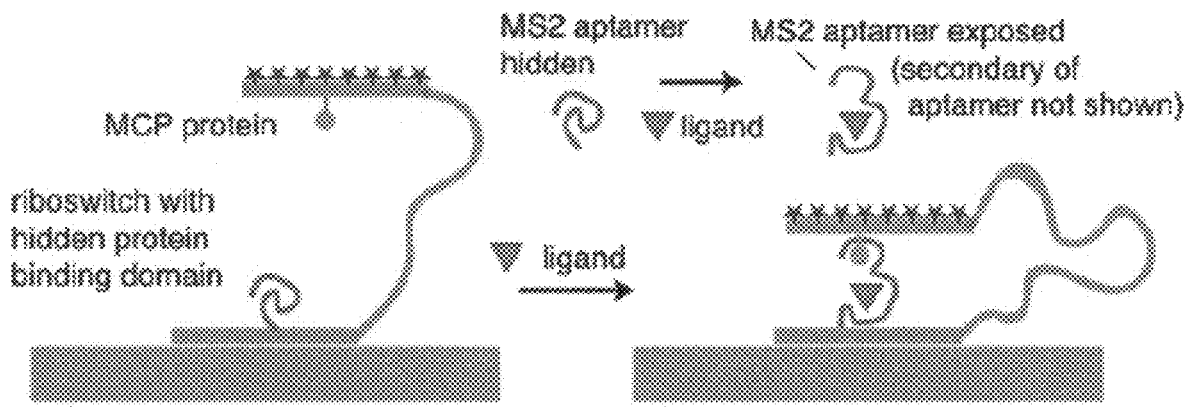

Accordingly, in one embodiment of the functional actuation mechanism enables the detection and concentration measurement small molecule targets via a change in the conformation of a 'riboswitch'. RNA and DNA aptamers can be selected by artificial molecular evolution (SELEX) to bind small molecule targets of interest. But (A) such targets are typically too small to be detected by a sandwich actuation mechanism, and (B) depending on the binding characteristics of a target and aptamer, a sensitive competitive actuation mechanism might be difficult to construct. In such cases the use of a functional actuation mechanism with a riboswitch may allow direct detection of a small molecule without competition. In such embodiments the aptamer is modified to become a riboswitch so that, upon binding of the small molecule target, it undergoes a conformational change to expose either a DNA or RNA sequence (FIG. 5A), or an RNA-protein (FIG. 5B) or DNA-protein binding domain. Thus the riboswitch can be used as one functional partner, and a protein, DNA, or RNA molecule can be used as the second functional partner. In particular, some embodiments may use an RNA riboswitch which exposes a commonly used MS2 aptamer upon binding the target small molecule, wherein the MS2 aptamer subsequently binds an MS2-viral major-coat-protein (MCP) attached to the other lid (FIG. 5B.)

Figure 5C:
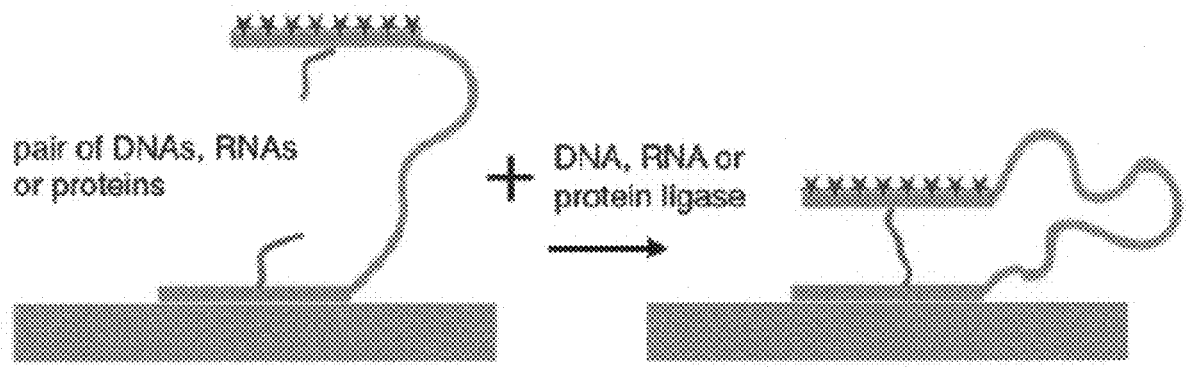

Accordingly, in one embodiment of the functional actuation mechanism, chemical or enzymatic ligation (joining or coupling) of two proteins, two nucleic acids or hybrids thereof are detected (FIG. 5C). In such an embodiment, functional partner 1 and functional partner 2 are the two molecules whose ligation is to be measured. Introduction of a chemical or enzymatic ligation agent will cause functional partners 1 and 2 to be covalently bonded together, consequently causing the sensor to close and generate signal. In such embodiments, it is the presence or absence, strength of activity, or concentration of the ligating agent that is being measured.

Figure 5D:
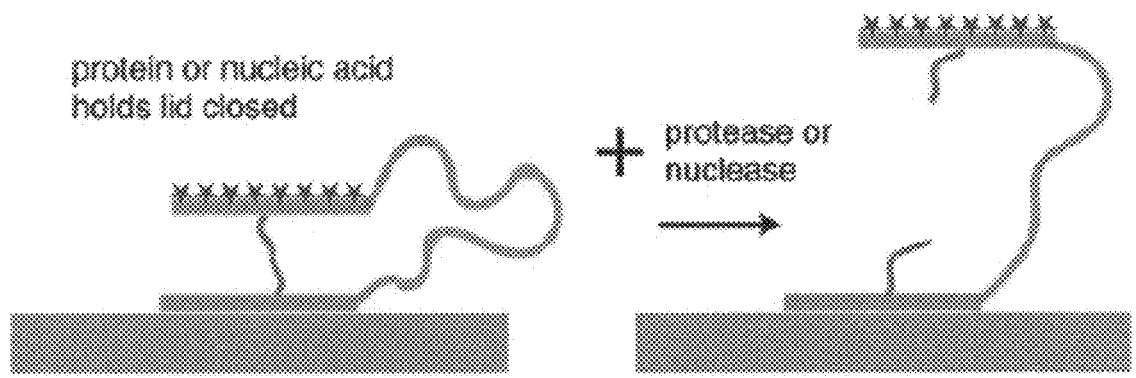

In a related embodiment of the functional actuation mechanism, chemical or enzymatic cleavage (cutting) of a protein or DNA is detected (FIG. 5D). Such embodiments present the reverse situation from that of the embodiment involving ligation. In such in embodiment functional partner 1 and functional partner 2 are prepared in a state such that they are exist as a single conjoined entity or are pre-ligated before measurement. Introduction of a chemical or enzymatic cleavage agent will separate functional partner 1 and functional partner 2 from each other, thus causing the sensor to open, generating signal. In such embodiments, it is the presence or absence, strength of activity, or concentration of the cleavage agent that is being measured.

Some embodiments of the invention may be enhanced by the use cooperativity. Cooperativity may be added to a sandwich (FIG. 4D), competitive, or functionally actuated sensor by increasing the number of binding partners, competitors, or functional partners that are present on the top and bottom lids of the sensor.

Embodiments in which the bistable molecular sensor is immobilized on a surface may be read out electronically or optically, using one of several widely known detection modalities. FIG. 6 illustrates the three different device architectures which may be used for embodiments on surfaces which read out the bistable molecular sensor electronically.

Figure 6A:
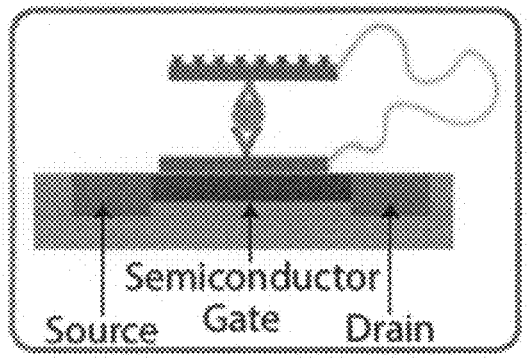
FIGS. 6A-C depict three different approaches to the electronic detection of the actuation of a bistable sensor immobilized on a surface.

In FIG. 6A, a bistable molecular sensor is immobilized on top of the gate region of a standard planar semiconductors transistor. Here, the sensor being in its "open" or "closed" state effects the local ionic-environment around the gate of the transistor in a manner that is quantifiable from the transistor characteristics. For instance, the transistor can be biased such that the sensor being in "open" or "closed" state directly leads to the transistor being switched "on" or "off".

Biosensing FETs constructed from classical semiconductor materials have been previously described (Veigas et al, "Field Effect Sensors for Nucleic Acid Detection: Recent Advances and Future Perspectives" Sensors 15 (2015): 10380-10398)

Figure 6B:
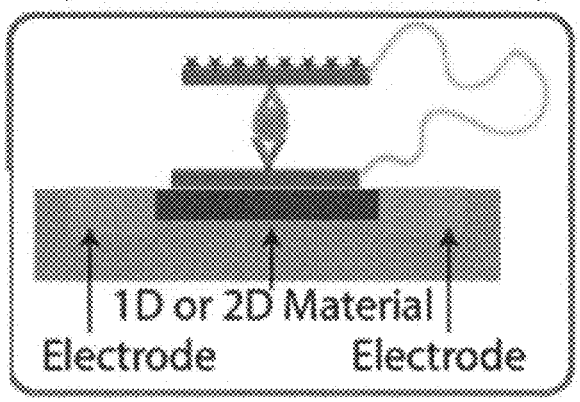

In FIG. 6B, the bistable molecular sensor is immobilized on the channel region of field effect transistor (FET) constructed from a low dimensional material such as a one-dimensional (1D) material (carbon nanotubes or silicon nanowires) or a two-dimensional (2D) material (graphene, molybdenum disulfide [$MoS_2$], or a thin layer of indium oxide). Here, the FET is composed of a channel, made from a 1D or 2D-material, between two electrodes with a gate contact (in the solution) to modulate the electronic response of the channel. The sensor being in its "open" or "closed" state effects the local ionic-environment around the gate of the transistor that is quantifiable from the transistor characteristics. For instance, the transistor can be biased such that the sensor being in "open" or "closed" state directly leads to the transistor being switched "on" or "off".

Biosensing FETs constructed from low dimensional materials have been described previously for: carbon nanotubes (Allen et al, "Carbon Nanotube Field-Effect-Transistor-Based Biosensors" Advanced Materials 19 (2007) 1439-1451); silicon nanowires (Chen et al, "Silicon nanowire field-effect transistor-based biosensors for biomedical diagnosis and cellular recording investigation" Nanotoday 6 (2011) 131-154); graphene (Afsahi et al, "Towards Novel Graphene-Enabled Diagnostic Assays with Improved Signal-to-Noise Ratio" MRS Advances 60 (2017) 3733-3739); molybdenum disulfide (Sarkar et al, "$MoS_2$ Field-Effect Transistor for Next-Generation Label-Free Biosensors", ACS Nano 8 (2014) 3992-4003) and indium oxide (Nakatsuka, et al, "Aptamer-field-effect transistors overcome Debye length limitations for small-molecule sensing", Science 6 (2018) eaao6750).

Figure 6C:
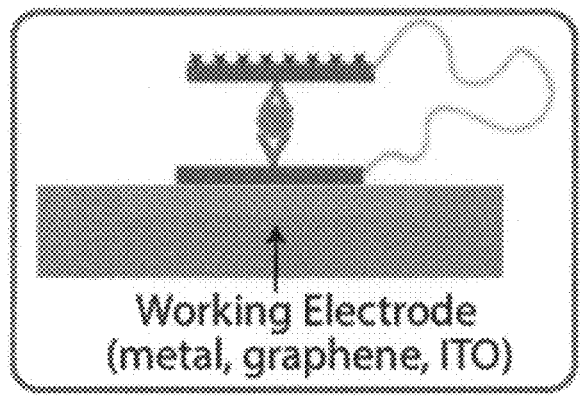

In FIG. 6C, the bistable molecular sensor is immobilized on top of a planar electrode, composed of a material of appropriate conductivity such as a metal (e.g. gold or platinum), graphene, indium tin oxide, or indium oxide. Here, the lid of the bistable molecular sensor carries a redox active molecule whose proximity to the electrode, in the "open" or "close" state, leads to transfer of electrons detectable as a current flow within the metal electrode. Electrochemical detection of bistable sensor actuation is performed using one of several widely known methods, including but not limited to: square wave voltammetry, cyclic voltammetry, electrochemical impedance spectroscopy, or chronoamperometry.

In one embodiment, electrochemical detection is performed on a gold electrode, where the gold surface has been prepared by electron beam deposition, or template-stripping from an ultraflat template such as mica or a silicon wafer, the redox active molecules on the top lid of the bistable sensor are methylene blue reporter molecules, the bottom lid of the bistable sensor is immobilized on the gold surface via thiol modifications, phosphorothioate modifications to the polynucleotide backbone, or polyadenosine extensions, and the gold electrode is otherwise covered by a self-assembled monolayer of mercaptohexanol (or a similar alkanethiol), which prevents undesired electrochemical reactions from obscuring the desired signal from the methylene blue molecules. In such an embodiment, closure of the bistable sensor will result in an increase in electron transfer rate from the methylene blue to the surface, creating "signal-on" behavior for the system. In some embodiments the change in electron transfer rate will be measured by square wave voltammetry.

Combinations of gold electrodes, methylene blue redox reporters, and alkanethiol passivation layers, read out by square wave voltammetry, are common in the literature, as previously described (Ricci et al, "Linear, redox modified DNA probes as electrochemical DNA sensors" Chemical Communications 36(2007): 3768-3770).

FIG. 7 illustrates the three different device architectures which may be used for embodiments on surfaces which read out the bistable molecular sensor optically.

Figure 7A:
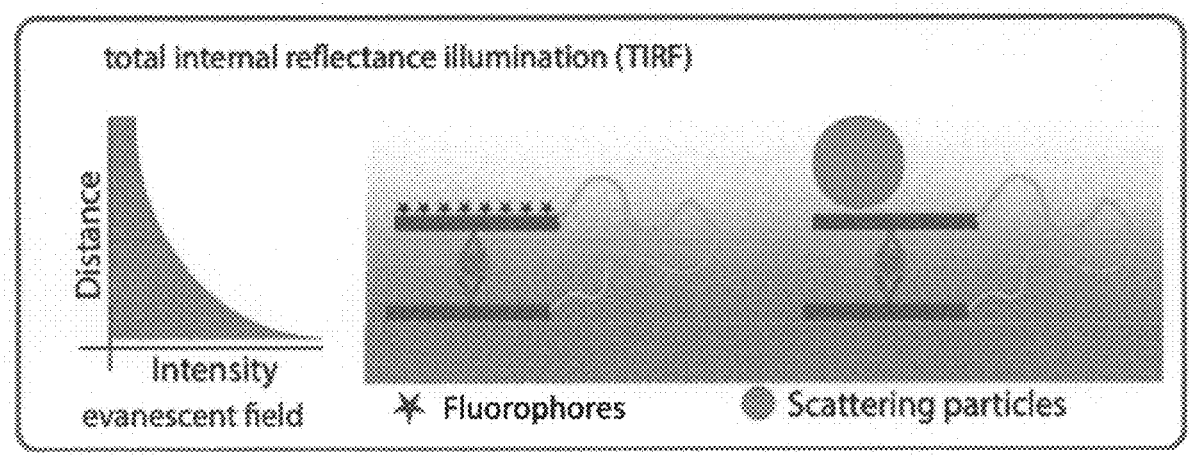
FIGS. 7A-E depict three different approaches to the optical detection of the actuation of a bistable sensor immobilized on a surface, including cartoon sketches of signal traces for both signal-on and signal-off embodiments.

In FIG. 7A, the bistable molecular sensor is immobilized on a transparent optical substrate (glass, quartz, silicon dioxide), and total internal reflectance illumination (TIRF illumination, wherein light below a critical angle is confined to propagate within the substrate) is used to generate an evanescent field at the surface. In such embodiments, optical reporters such as light emitters (e.g. organic fluorophores or quantum dots) or light scatters (such as 25-50 nanometer plasmonic particles, or 500 nm to 1 micron dielectric particles) are attached to the top lid. In the open state the optical reporters will be far enough away from the surface that a small fluorescence or scattering signal is observed. In some embodiments plasmonic nanoparticles are gold or silver nanoparticles. In some embodiments, dielectric particles are silica or polystyrene nanospheres. In the closed state optical reporters will be in the strong part of the evanescent field so that a large fluorescence or scattering signal is observed. The distance dependent decay of the evanescent field is related to the wavelength lambda of light produced by the emitters or scattered by the particles, with the critical distance for a strong signal being typically lambda/10. The use of single origami for TIRF optical measurements has been previously described (Gietl et al "DNA origami as biocompatible surface to match single-molecule and ensemble experiments" Nucleic Acids Res. 40 (2012): e110 and Tsukanov et al, "Detailed study of DNA hairpin dynamics using single-molecule fluorescence assisted by DNA origami", Phys. Chem. B 117 (2013):11932-11942).

Figure 7B:
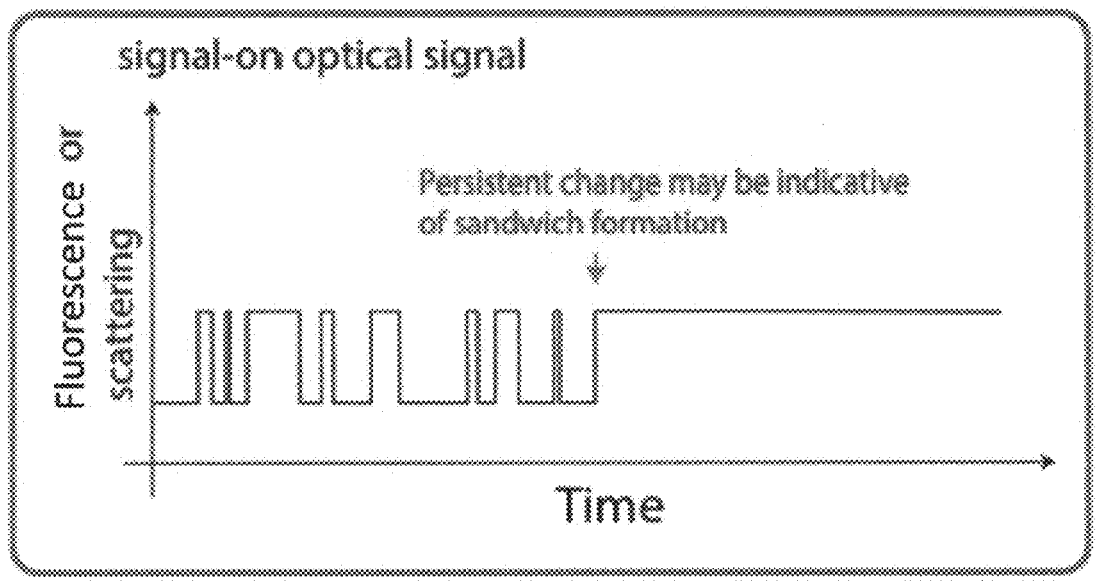
Figure 7C:
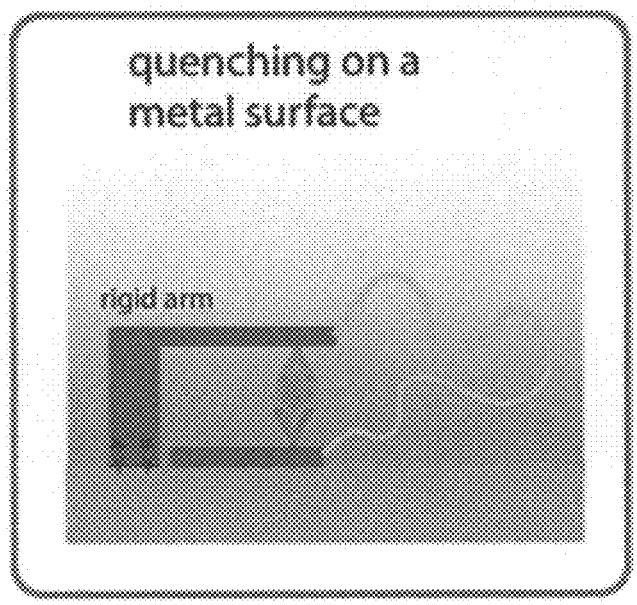

In FIG. 7C, the bistable sensor is immobilized on a substrate (gold, or graphene) which strongly quenches the fluorescence of a light emitter, as has been described for gold (Dulkeith et al, "Gold Nanoparticles Quench Fluorescence by Phase Induced Radiative Rate Suppression" Nano Letters 5 (2005):585-589) and graphene (Kasry et al, "Highly Efficient Fluorescence Quenching with Graphene" J. Phys. Chem. C 116 (2012):2858-2862). Accordingly, in the open state, optical signal from the top lid of the bistable sensor is large, and in the closed state, optical signal from the top lid of the bistable sensor is much smaller. In such embodiments, the strongest quenching effect is observed when the emitters are within a few nanometers of the surface, and accordingly such embodiments may use a bistable device geometry wherein signal molecules on the top lid are positioned rigidly and in intimate contact (less than a few nanometers) from the surface. One such potential geometry is diagrammed in FIG. 7C, in particular a top lid with a rigid arm that extends out beyond the area of the bottom lid.

Figure 7D:
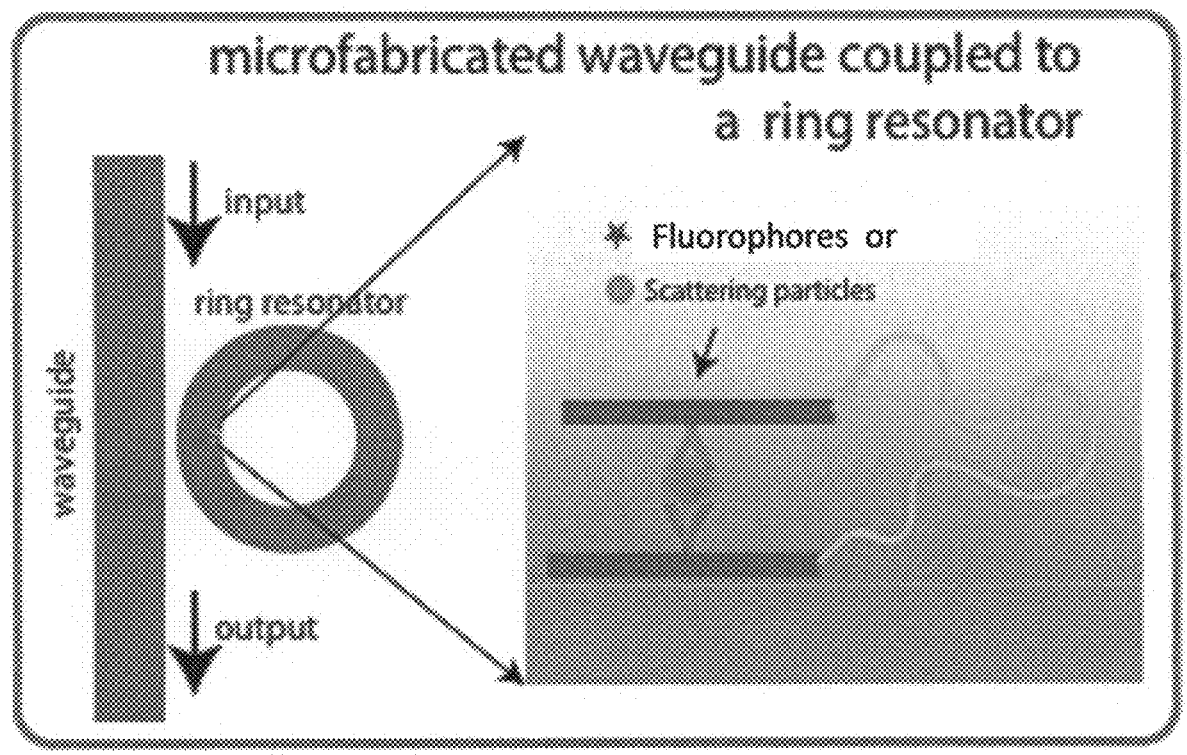

In FIG. 7D, the bistable sensor is immobilized on a microfabricated ring resonator (as described in Sarkaleh et al, "Optical Ring Resonators: A Platform for Biological Sensing Applications" J. Med. Signals. Sens. 7 (2017):185-191) using a widely known DNA origami placement technology, wherein the microfabricated ring resonator is strongly coupled strongly to an optical waveguide. In such embodiments, light emitters or optical scatters are both compatible optical reporters of the state change of the bistable sensor. Excitation light input to one end of the waveguide enters the ring resonator, and may or may not be emitted as fluorescence or scattered by reporters on the lid of the bistable device. If the bistable device is open, then light circulating in the ring simply returns to the waveguide, and is observed at the output as a transmitted signal. If on the other hand, the bistable device is closed, the light circulating in the ring resonator is either converted into longer wavelength emission light (in the case the reporter is a light emitter) or scattered away (in the case the reporter is an optical scatter). Thus when the device is closed, a decreased amount of light is returned from the ring to the waveguide, and a decreased transmission of signal is measured at the waveguide output. For such embodiments, the position of the lid in the closed state can be up to 50 nanometers away from the surface of the ring resonator.

Figure 7E:
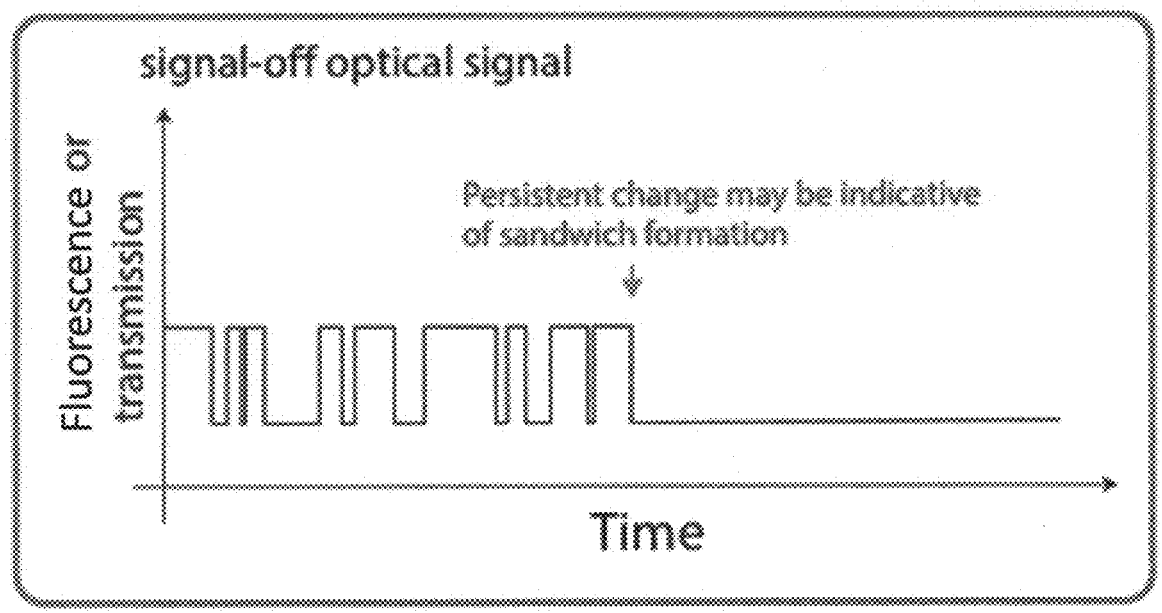

For embodiments such as those diagrammed in FIG. 7A, the measured optical signal increases upon closing of the bistable sensor, yielding a so-called "signal-on" detection modality (FIG. 7B). For embodiments such as those diagrammed in FIGS. 7C, and 7D, the measured optical signal decreases upon closing of the bistable sensor, yielding a so-called "signal-off" detection (FIG. 7E).

In other embodiments of optical surface readout, bistable sensors are immobilized on other types of microfabricated optical devices using widely known DNA origami placement technology. In some embodiments, bistable sensors with light emitters are positioned in the center of a metal (e.g. gold) optical bowtie antenna. The strong electric field at the center of such bowtie antennas is known to enhance the fluorescence of light emitters (as described in Kinkhabwala, et al. "Large single-molecule fluorescence enhancements produced by a bowtie nanoantenna", Nature Photonics 3 (2009):654-657). Thus in such embodiments the closed state of the bistable sensor will exhibit enhanced light emission yielding a system with "signal-on" behavior. For such embodiments, the position of the lid in the closed state will have to be within a few nanometers of the center of the bowtie for maximum optical signal.

In other embodiments of optical surface readout, bistable sensors are immobilized within photonic crystal cavities (PCC) using widely known DNA origami placement technology. As has been demonstrated previously described (Gopinath et al, "Engineering and mapping nanocavity emission via precision placement of DNA origami", Nature 535 (2016): 401-405), the interaction emitters on the DNA origami with the PCC depends strongly on the nanometer-scale positioning relative to nodes within the PCC's resonant mode. At some positions, as can be accurately predicted by finite-difference time-domain (FDTD) analysis, the coupling between an emitter and the cavity can be weak, and at other positions it can be strong. For bistable devices placed appropriately at peaks within the optical resonant mode of PCC, optical signal will be enhanced when the bistable device closes, yielding a system with "signal-on" behavior.

For some embodiments of surface-based optical detection, readout of the bistable sensor is achieved by measuring the polarization in an epifluorescence microscope. For such embodiments, anisotropic gold rods are used as the optical reporter on the top lid of the origami. Accordingly, when the bistable sensor closes and top lid is bound, the gold rod switches from a freely rotating condition to being fixed in a particular orientation. This change in rotational diffusion of the gold rod is easily detected with an epifluorescence microscope by examining light scattered from the rod with at two different polarizations and calculating the ratio between them. Ratios close to one are indicative of bistable sensors in the open state, and ratios far from one are indicative of bistable sensors in the closed state. Embodiments using linear polarization comprise a single anisotropic nanorods on the top lid of the origami. Embodiments using circular polarization comprise a pair of nanorods, with one being on the top lid, and one being on the bottom lid of the origami. Two-nanorod systems using circularly polarized light have been described (Zhou et al. "A plasmonic nanorod that walks on DNA origam" Nature Communications 6 (2015):8102).

Embodiments of surface-based readout of bistable sensors may produce both analog or digital signals. In some embodiments, optical or electronic measurements are taken over larger areas, which comprise large numbers of biosensors, and so such measurements provide a sum of signals for a large number of sensors. In such embodiments, single biosensor behavior will be averaged out, and the readout will be analog in nature.

However, in some embodiments, the discrete nature of bistable sensors and the signal amplification potentially provided by the large polynucleotide lid and large number of signaling molecules enables measurement of discrete single molecule events. In some embodiments, such single-molecule measurements are further enabled by the ability to position individual bistable sensors into grids using DNA origami placement. In such embodiments readout will be digital in nature, as depicted in the time/signal traces in FIG. 7B, FIG. 7E and FIG. 10. Some optical embodiments enable the simultaneous digital measurement of thousands of bistable sensors, for example over an entire microscope field in the context of TIRF microscopy as is commonly practiced in single molecule biophysics. Some electronic embodiments may achieve digital, single-molecule electronic measurements, for example in the case that DNA origami placement is used to position a bistable sensor between two electrodes to take advantage of single-molecule redox-cycling (as described in Lemay et al, "Single-Molecule Electrochemistry: Present Status and Outlook" Acc. Chem. Res. 46 (2013): 369-377).

Embodiments that achieve single-molecule digital measurement of bistable sensors will be able to observe fluctuations in the state of bistable sensors, as depicted for early times in the time/signal traces in FIG. 7B, FIG. 7E and FIG. 10. Bistable sensor in the open state will fluctuate between situations in which the top lid is far from the surface, and situations in which the top lid is near the surface. Depending on the length of the linker, and diffusion constant of the top lid, this fluctuation will have a characteristic time constant $T_1$ that dictates switching between "on" and "off" states in the signal trace. Upon detection of the molecular event, whether it is a binding event, or other event such as a modification, the top and bottom lids of the bistable sensor will at least have a greater affinity for each other, so that fluctuations the of a bistable sensor have a different characteristic time constant $T_2$ with $T_2$ being greater than $T_1$.

The greater the difference between $T_2$ and $T_1$, the more easily a molecular event can be detected. In the limit that the molecular event causes the top lid to have a neglibible off-rate (because its affinity for the bottom lid is extremely high), the closed state will be stable and irreversible. In this limit, a binding event or other molecular will cause a persistent change in the time/signal trace of a single molecule measurement, as is depicted for later times in FIG. 7B, FIG. 7E and FIG. 10. This limit of strong binding and irreversible change to the bistable sensor was diagrammed for clarity, but will hold for many embodiments. In many embodiments, the binding of a target molecule, or modification of functional molecule within the sensor will not result in an irreversible change, the time/signal trace will change its rate of fluctuation, and detection of the molecular event will have to be inferred from this rate change.

Different embodiments of bistable sensors employ lids having different shapes (FIG. 8), as dictated by the requirements for maximizing performance of the particular surface-based read-out mechanism, and the characteristics (e.g. size, shape) of the functional molecules used (e.g. antibodies, aptamers). Among many possible geometries, four are diagrammed in FIG. 8: (A) A simple version where both bottom and top lid are identically shaped; (B) a version in which the bottom lid has a window such that signaling molecules on the top lid can come in contact with the surface, thereby ensuring maximum signal upon formation of a stable "closed" state; origami with such a window are previously described (Rothemund, Paul W K. "Folding DNA to create nanoscale shapes and patterns", Nature 440.7082 (2006): 297 and patent application 161284/CIT-7845, U.S. Ser. No. 16/121,603; (C) a version in which the top lid is designed to be asymmetric, with rigid arm that ensures intimate, stable contact of the top lid and any signal molecules it carries with the substrate; (D) a version in which the top lid is designed to be a 3D hemisphere or dome, whose edge has a radius that extends beyond the radius of the bottom lid, which both ensures intimate contact of the top lid and signal molecules with the surface and further allows the bistable sensor to accommodate binding molecules of a large size (for example a pair of two antibodies with a large antigen). DNA with such hemisphere or dome shapes have been previously described (Han et al, "DNA origami with complex curvatures in three-dimensional space", Science 332 (2011): 342-346)

Figure 8A:
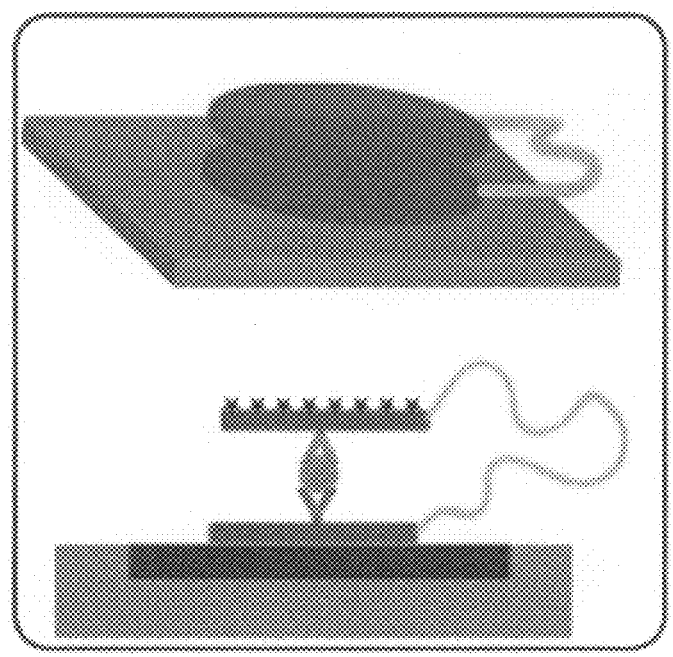
FIGS. 8A-D depict four different geometries for bistable sensors, each presenting a different configuration of signal molecules or polynucleotide material to the underlying detector surface when the bistable sensor is in its closed state.
Figure 8B:
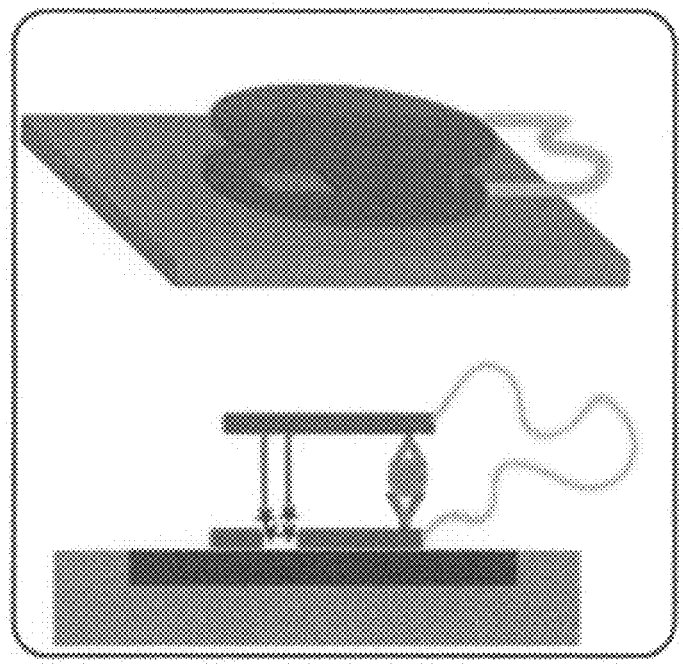
Figure 8C:
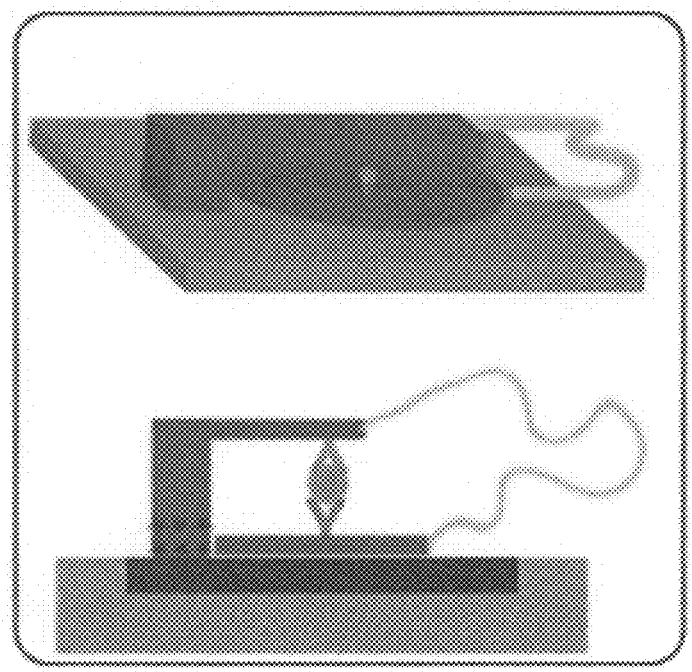
Figure 8D:
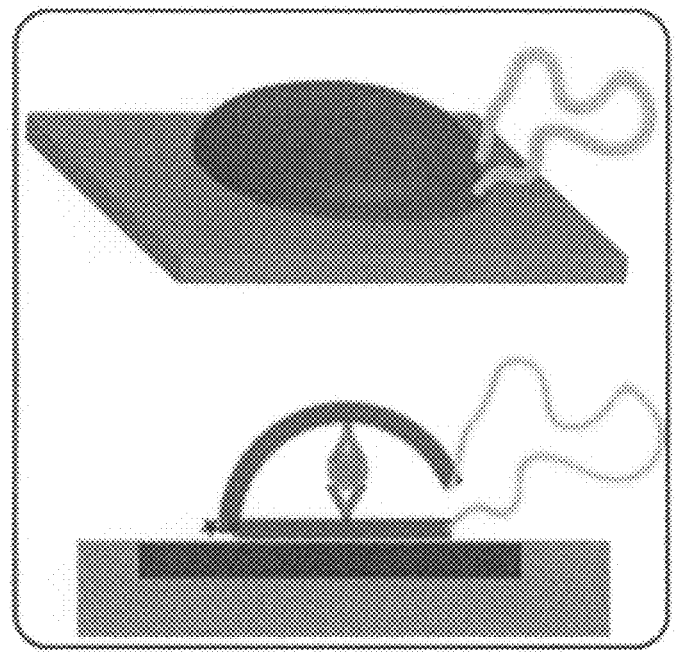

Performance as a function of bistable device geometry, depends on the particular embodiment. The geometry diagrammed in FIG. 8A is suitable for embodiments which utilize TIRF microscopy (FIG. 7A) for which the light-emitting or scattering signal molecules do not need to get very close to the surface to create a large signal. Strong signals in such embodiments may be observed for top lid-to-surface distances of lambda/10 where lambda is the wavelength of light used. Thus for green light with lambda equal to 532 nm, strong signals are achieved within 50 nm of the surface, where the top lid will be within the strong portion of the evanescent field. The coupling of light emitters on the lid of a bistable device to a microfabricated optical cavity (FIG. 7D) will also be strong for top lid-to-surface distances of lambda/10. Accordingly, embodiments which use microfabricated cavities to enhance optical detection by scattering or fluorescence may achieve high performance using the simple geometry diagrammed in FIG. 8A.

Maximum quenching on a metal (FIG. 7C), maximum disturbances to the capacitance of a gate (FIG. 6A and FIG. 6B), and maximum electron transfer rates in electrochemical settings (FIG. 6C) are typically observed within 2 nanometers of a surface. Accordingly, embodiments which use optical sensing based on quenching (FIG. 7C), as well as embodiments which use field effect sensing (FIG. 6A and FIG. 6B), as well as embodiments which use electrochemical sensing (FIG. 6C) may all benefit from device geometries which enable more intimate contact of the top lid and the signal molecules it may carry with the surface, for example the bistable device geometries diagrammed in FIG. 8B, FIG. 8C, and FIG. 8D.

Figure 9A:
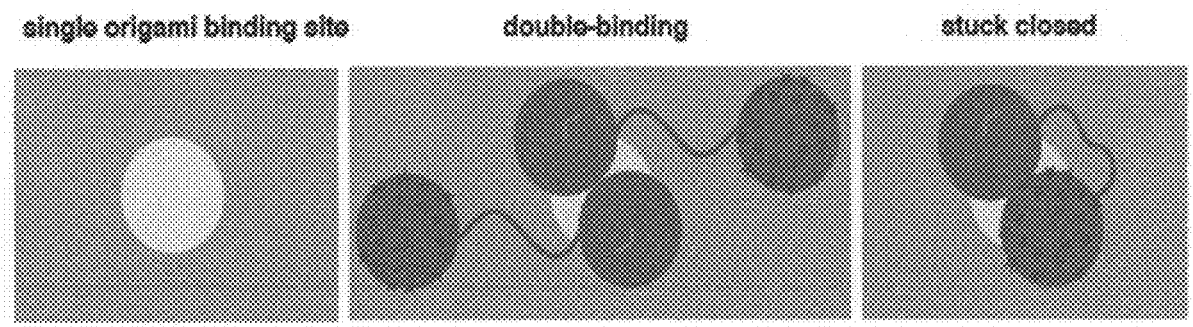
FIGS. 9A-9C depict problems and solutions for surface placement of bistable sensors on optical or electronic surfaces.
Figure 9B:
Figure 9C:
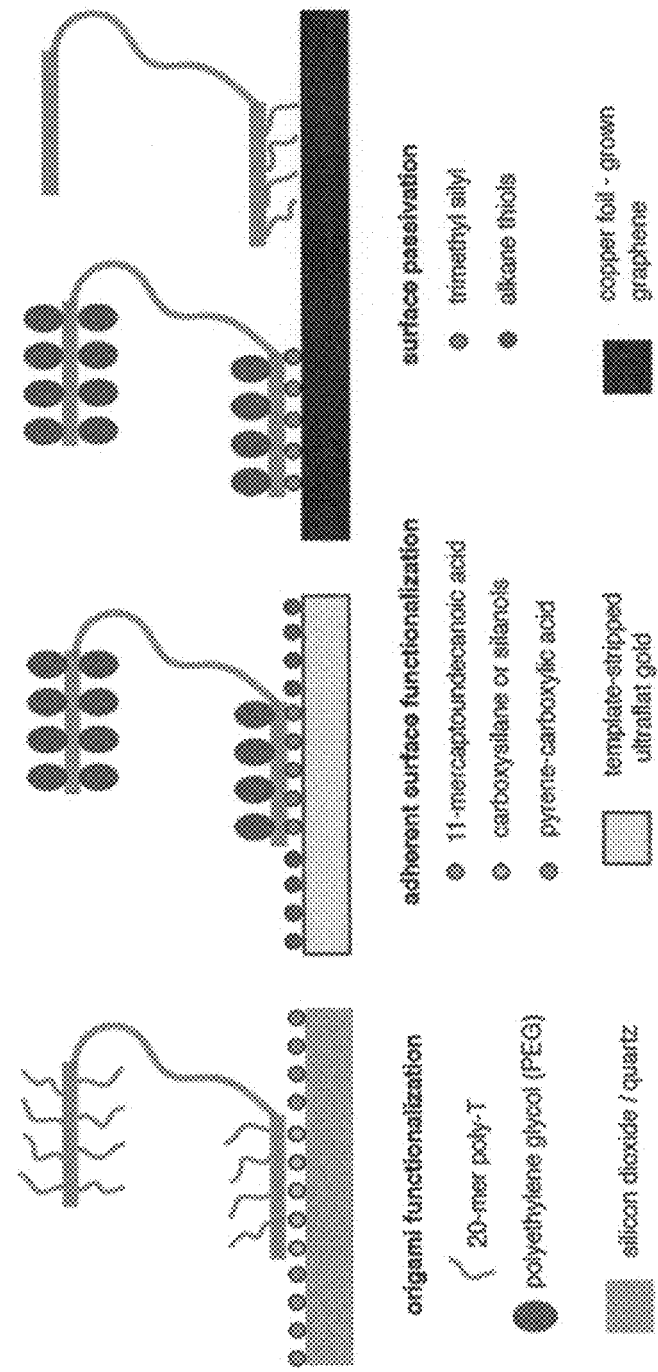

Performance of the flytraps on a surface is subject to a number of potential problems not present in solution, which in different embodiments are solved by adjusting the surface chemistry of the substrate, and the different components of the bistable sensor, as shown in FIGS. 9A-9C.

For example, one lid of the fly trap must be immobilized on the surface (the bottom lid), and the other (the top lid) must be free floating in solution. If the top lid has too high an affinity for the surface, it will stick next to the bottom lid and it may appear that the flytrap has bound and detected a target molecule (a false positive). Such problems arise on unpatterned surfaces, as well as surfaces patterned with DNA origami binding sites (FIG. 9A). Empty sites, double bindings, and sensors stuck closed are all problems which can be caused by improper adhesion of a bistable sensor to the surface.

The ability to control adhesion of origami for surfaces is most well-developed on silicon nitride and silicon dioxide substrates (as described in Kershner et al, "Placement and orientation of individual DNA shapes on lithographically patterned surfaces", Nature Nanotechnology 4 (2009):557-561; Hung et al, "Large-area spatially ordered arrays of gold nanoparticles directed by lithographically confined DNA origami", Nature Nanotechnology 5 (2010): 121-126; Gopinath et al, "Optimized Assembly and Covalent Coupling of Single-Molecule DNA Origami Nanoarrays", ACS Nano 8 (2014):12030-12040; and Gopinath et al, "Engineering and mapping nanocavity emission via precision placement of DNA origami", Nature 535 (2016): 401-405). FIG. 9C diagrams one embodiment for properly binding flytraps substrates which have an appropriate surface oxide, such as silicon dioxide, quartz, and silicon nitride. In side view one can see that there are five distinct regions to a flytrap which must have the appropriate stickiness, or non-stickiness to the surface for the flytrap to be oriented properly: both surfaces of the top lid must not adhere to the negatively charged silanol/carboxysilane binding site or surrounding trimethyl silyl background (created via hexamethyldisilazane [HMDS] vapor deposition), the linker between the lids must not stick to the binding site or background, one surface of the bottom lid must not stick, and one surface of the bottom lid must stick to the binding site. At the experimental conditions commonly used (having 10 mM $Mg^{2+}$ ions) flat, disk-shaped origami stick strongly to binding sites, because a layer of $Mg^{2+}$ ions provides a bridge between negatively charged surface sites and the negatively charged origami surface. On the other hand, linear double-stranded DNAs, such as some embodiments of the linker do not, as shown experimentally by their movement under atomic force microscopy. Other work (as described in patent application 161284/CIT-7845) teaches how to render one side of a DNA origami nonsticky for a negatively charged binding site by adding a layer of 20-mer poly-T single-stranded DNA hairs. This modification is highly effective on silicon dioxide: when origami which have one flat side and one hairy side are deposited, more than 98% of the origami bind with the flat side facing the surface. Accordingly, in some embodiments, the three faces of the flytrap disks can be functionalized with DNA hairs to provide the appropriate orientation.

In some embodiments, on different substrate materials, other solutions to the problem of preventing the top lid from sticking to the background may be required. The bottom lid constrains the top lid to be permanently adjacent to the surface, via the linker. This gives the top lid a high local concentration, which shifts the equilibrium for weak interactions and/or may allow alternative binding mechanisms time enough to occur. For some embodiments wherein the top lids of flytraps stick to the surface, the top lids may be rendered less sticky by changing their shape and decreasing their surface area, for example by implementing them as 6-helix bundles as in FIG. 9B. This approach has a clear effect on mica, where 6-helix bundles and other 3D origami are much less adherent to the surface than flat origami of higher surface area. For some embodiments wherein electronic sensing is used, this solution may come at the cost of decreasing sensitivity since it will decrease the mass of origami and/or number of signaling molecules close to the sensor surface.

For some embodiments employing gold electrodes (FIG. 9C), it is possible to closely mimic the silicon dioxide system, where adhesion may be tuned by $Mg^{2+}$ concentration. Ultra-flat template-stripped gold with an RMS roughness of 3.6 angstroms (comparable to a silicon dioxide wafer) may be used as a substrate. To create negatively-charged binding sites analogous to those available on silicon dioxide, carboxylated thiols such as 11-mercaptoundecanoic acid, are used to create a self-assembled monolayer. Such monolayers have previously been used to adhere origami to gold in the presence of $Mg^{2+}$ ions as previously described (Gerdon et al, "Controlled Delivery of DNA Origami on Patterned Surfaces", Small 5 (2009): 1942-1946). The non-adherent background can be implemented using alkanethiols chosen to give a self-assembled monolayer with a contact angle that is similar to that generated by HMDS on silicon dioxide.

Other embodiments employing gold electrodes use polyadenosine (polyA) strand extensions, thiol-labels, or phosphorothioate backbones on DNA origami to provide adhesion for the bottom lid of the flytrap to the gold. DNA adhesion based on thiols, phosphorothioate, and polyadenosine strands has been previously described (Zhou et al, "Tandem phosphorothioate modifications for DNA adsorption strength and polarity control on gold nanoparticles." ACS Applied Materials Interfaces 6 (2014):14795-147800). Anti-adhesion between the top lid and the background surface may be provided by the use of polyethylene glycol or dextran modifications to the top lid, as well as polyethylene-glycol-thiol modifications to the background on the gold substrate.

For some embodiments employing graphene FET surfaces, the silicon dioxide system can be mimicked to provide $Mg^{2+}$-driven adhesion through the use of pyrene-carboxylic acid molecules that bind strongly to graphene (FIG. 9C). For some such embodiments, carboxylic acid-modified graphene may bind DNA origami nonspecifically, and PEGs may be added to the nonadherent flytrap surfaces.

However, because double-stranded DNA does not stick strongly to graphene surfaces, and the exposed hydrophobic bases of single-stranded DNA do stick strongly to graphene, other choices open up for managing adhesion on graphene. Accordingly, in some embodiments unpatterned unmodified graphene, may be used. In such embodiments, single-stranded DNA (e.g. poly-thymine [polyT]) may be added to the adherent flytrap surface on the bottom lid (FIG. 9C); in such embodiments the other surfaces of the flytrap will have very low adhesion to the unmodified graphene. A similar single-stranded linker strategy has been used to attach carbon nanotubes to DNA origami (Maune et al, "Self-assembly of carbon nanotubes into two-dimensional geometries using DNA origami templates" Nature Nanotechnology (2010) 61-66) to form field-effect transistors.

For surface-based embodiments, multiplexing of distinct bistable sensors can be accomplished by independently synthesizing sensors with specificities to different target molecules, or sensitivities to different functionalities in separate test tubes and spatially positioning the distinct sensors into an array onto a surface suitable for optical or electronic detection. Spatial positioning can be accomplished at the microscale using a variety of technologies including ink-jet printing and microarray printing (as described in Barbulovic-Nad et al "Bio-microarray fabrication techniques—a review." Critical Reviews in Biotechnology. 26 (2006):237-59.) Accordingly, for surface based embodiments, microscale spotting creates arrays suitable for analog measurements of summed bistable device behavior, wherein each spot contains a multiplicity of randomly-arranged bistable devices; in some embodiments each spot contains at least 10 bistable devices.

For surface-based embodiments, single-molecule arrays suitable for single molecule optical or electronic detection can be constructed lithographically, using the technique of DNA origami placement, as described in references above. The construction of 65,536 optical devices (Gopinath et al, "Engineering and mapping nanocavity emission via precision placement of DNA origami", Nature 535 (2016): 401-405), wherein each device was a 5 micron by 5 micron area containing a photonic crystal cavity, and wherein each device had a deterministically defined number of individual DNA origami positioned within it, where the number ranged programmatically from zero to seven, is particularly relevant. Thus in some embodiments (FIG. 10), microscale spotting can be combined with DNA origami placement to achieve a perfectly regular array of single-molecule single-bistable sensor arrays, wherein each of N arrays is specific for a particular analyte, and within each of the N arrays, there are M binding sites for single bistable devices that are filled with exactly one bistable sensor with a probability greater than 95%. Based on the number of individual binding sites which have been created, some embodiments have arrays comprising a total number of spots N times M equaling up to 100,000. Some embodiments have up to 1000 arrays, each with at least 10 binding sites for bistable devices.

Multiplexed electronic detection has been accomplished for over 4000 CMOS electrochemical sensors (as described in Sun et al "A scalable high-density electrochemical biosensor array for parallelized point-of-care diagnostics", 2015 IEEE Biomedical Circuits and Systems Conference, IEEE Journal of Solid-State Circuits 53 (2018) 2054-2064). Accordingly, some embodiments combine microarray spotting with electronic devices to achieve multiplexed arrays of up to 4000 distinct types of bistable devices, wherein each spot is printed on a microscale electronic device, each spot contains a multiplicity of randomly arranged bistable sensors, and readout from each microscale electronic device is the summed response of the multiplicity of bistable sensors; in some embodiments each spot contains at least 10 bistable devices.

What is claimed is:

1. A structure comprising a bistable molecular sensor for multiplexed detection of external stimuli, the bistable molecular sensor comprising a nucleic acid structure, comprising:

a first polynucleotide shape and a second polynucleotide shape with a flexible hinge or flexible linker therebetween, the first polynucleotide shape comprising a first shape inside surface and a first shape outside surface and the second polynucleotide shape comprising a second shape inside surface and a second shape outside surface, the first shape inside surface being capable of facing the second shape inside surface; and one or more functional molecules bound to at least one of the first polynucleotide shape and the second polynucleotide shape, the bistable molecular sensor having one of two states, the two states being a closed state and an open state, wherein:

in the open state, the first polynucleotide shape moves freely with respect to the second polynucleotide shape as constrained by the flexible hinge or flexible linker; and in the closed state, the first polynucleotide shape is proximally positioned to the second polynucleotide shape, wherein the one or more functional molecules further comprise:
 a first actuation molecule; and
 a second actuation molecule, wherein an actuation mechanism of the bistable molecular sensor is configured such that a molecular event involving the first and second actuation molecules shifts an equilibrium conformation of the bistable molecular sensor towards the closed state, and wherein the one or more functional molecules further comprise:
 a nucleotide barcode on at least one of the first shape outside surface and the second shape outside surface, wherein the nucleotide barcode is configured to be read out; and
 an affinity tag positioned on at least one of the first shape inside surface and the second shape inside surface, wherein the affinity tag is configured to bind to a separation device when the bistable molecular sensor is in the open state and to be sterically blocked when the bistable molecular sensor is in the closed state.

2. The structure of claim 1,
wherein
 the first and second actuation molecules of the one or more functional molecules comprise:
  a first binding molecule attached to the first shape inside surface; and
  a second binding molecule attached to the second shape inside surface, each of the first binding molecule and the second binding molecule being capable of binding a target molecule,
 wherein the molecular event comprises a binding event of the target molecule with the first binding molecule and the second binding molecule, such that the equilibrium conformation of the bistable molecular sensor shifts towards the closed state.

3. The structure of claim 1, wherein the nucleotide barcode comprises a restriction site sequence and is capable of being cleaved from the at least one of the first shape outside surface and the second shape outside surface by cleavage at the restriction site.

4. The structure of claim 1, wherein the nucleotide barcode comprises a nucleotide complex capable of strand displacement, wherein upon addition of a corresponding DNA or RNA strand, the nucleotide complex is released from the at least one of the first shape outside surface and the second shape outside surface.

5. A detection system comprising a plurality of the structures of claim 2, the plurality of structures comprising a plurality of bistable molecular sensors, wherein:
 the first binding molecule and the second binding molecule on each of the plurality of bistable molecular sensors are capable of binding to a different target molecule, and
 the nucleotide barcode on each of the plurality of bistable molecular sensors is unique for each of the different target molecules.

6. The detection system of claim 5, wherein the plurality of structures comprises:
 at least 8 different bistable molecular sensors;
 at least 8 different target molecules; and
 at least 8 different unique nucleotide barcodes.

7. The detection system of claim 5, wherein the plurality of structures comprises:
 at least 1,000 different bistable molecular sensors;
 at least 1,000 different target molecules; and
 at least 1,000 different unique nucleotide barcodes capable of being identified using next generation sequencing.

8. The structure of claim 1, wherein:
 the first and second actuation molecules of the one or more functional molecules comprise a first single-stranded nucleic acid and a second single-stranded nucleic acid, the first single-stranded nucleic acid and the second single-stranded nucleic acid being different from each other and complementary to a target single-stranded nucleic acid,
 one or more copies of the first single-stranded nucleic acid is attached to the first polynucleotide shape,
 one or more copies of the second single-stranded nucleic acid is attached to the second polynucleotide shape, and
 in the presence of the target single-stranded nucleic acid, the first single-stranded nucleic acid and the second single-stranded nucleic acid bind to target single-stranded nucleic acid, thereby shifting the equilibrium conformation of the bistable molecular sensor towards the closed state.

9. The structure of claim 1, wherein:
 the first and second actuation molecules of the functional molecules comprise a first CRISPR inactive enzyme guide RNA complex and a second CRISPR inactive enzyme guide RNA complex, the first CRISPR inactive enzyme guide RNA complex and the second CRISPR inactive enzyme guide RNA complex being different from each other and complementary to a target double-stranded nucleic acid,
 one or more copies of the first CRISPR inactive enzyme guide RNA complex is attached to the first polynucleotide shape,
 one or more copies of the second CRISPR inactive enzyme guide RNA complex is attached to the second polynucleotide shape, and
 in the presence of the target double-stranded nucleic acid, the first CRISPR inactive enzyme guide RNA complex and the second CRISPR inactive enzyme guide RNA are bound to the target double-stranded nucleic acid, thereby shifting the equilibrium conformation of the bistable molecular sensor towards the closed state.

10. The structure of claim 1, wherein:
 the first and second actuation molecules of the one or more functional molecules comprise an allosteric CRISPR inactive enzyme guide RNA complex and a complementary allosteric nucleic acid sequence, the allosteric CRISPR inactive enzyme guide RNA complex having a conditionally hidden allosteric nucleic acid sequence,
 the allosteric CRISPR inactive enzyme guide RNA complex capable of binding to a target double-stranded nucleic acid thereby exposing the conditionally hidden allosteric nucleic acid sequence,
 one or more copies of the allosteric CRISPR inactive enzyme guide RNA complex is attached to the first polynucleotide shape,
 one or more copies of the complementary allosteric nucleic acid sequence is attached to the second polynucleotide shape, and
 in the presence of the target double-stranded nucleic acid, the allosteric CRISPR inactive enzyme guide RNA complex is bound to the target double-stranded nucleic acid and the complementary allosteric nucleic acid sequence is bound to the exposed conditionally hidden allosteric nucleic acid sequence, thereby shifting the equilibrium conformation of the bistable molecular sensor towards the closed state.

11. The structure of claim 1, wherein:
the first and second actuation molecules of the one or more functional molecules comprise an antibody capable of binding a target molecule and a competitor molecule capable of binding the antibody in the absence of the target molecule,
one or more copies of the competitor molecule attached to the first polynucleotide shape,
one or more copies of the antibody attached to the second polynucleotide shape,
in the absence of the target molecule, the competitor molecule is bound to the antibody, thereby shifting the equilibrium conformation of the bistable molecular sensor towards the closed state, and
in the presence of the target molecule, the competitor molecule is displaced by the target molecule, thereby shifting the equilibrium conformation of the bistable molecular sensor towards the open state.

12. The structure of claim 1, wherein:
the first and second actuation molecules of the one or more functional molecules comprise a first protein capable of being chemically or enzymatically modified by a chemical or enzymatic agent resulting in a modified first protein and a second protein capable of binding the modified first protein,
one or more copies of the first protein are attached to the first polynucleotide shape,
one or more copies of the second protein are attached to the second polynucleotide shape, and
the molecular event chemically or enzymatically modifies the first protein and increases the affinity between the first and second proteins such that the equilibrium conformation of the bistable molecular sensor shifts towards the closed state.

13. The structure of claim 12, wherein the first protein is capable of being modified by at least one of phosphorylation, acetylation, ubiquitination, prenylation, adenylation, or glycosylation.

14. The structure of claim 13, wherein the second protein is a naturally occurring protein capable of binding the modified first protein.

15. The structure of claim 13, wherein the second protein is an antibody capable of binding to phosphorylation, acetylation, ubiquitination, prenylation, adenylation, or glycosylation.

16. The structure of claim 1, wherein:
the first and second actuation molecules of the one or more functional molecules comprise a capture nucleic acid and a capture molecule, the capture nucleic acid capable of being chemically or enzymatically modified by a chemical or enzymatic agent resulting in a modified capture nucleic acid and the capture molecule capable of binding the modified capture nucleic acid,
one or more copies of the capture nucleic acid are attached to the first polynucleotide shape,
one or more copies of the capture molecule are attached to the second polynucleotide shape,
in the presence of the chemical or enzymatic agent, the capture nucleic acid is modified resulting in the modified capture nucleic acid and the capture molecule is bound to the modified capture nucleic acid, thereby shifting the equilibrium conformation of the bistable molecular sensor towards the closed state.

17. The structure of claim 16, wherein the capture nucleic acid is capable of being modified by at least one of cytosine methylation, cytosine hydroxymethylation, cytosine formylation, cytosine carboxylation, adenosine methylation, alkylation, or thymine dimerization.

18. The structure of claim 17, wherein the capture molecule is a naturally occurring molecule capable of binding the capture nucleic acid.

19. The structure of claim 17, wherein the capture molecule is an antibody capable of binding to cytosine methylation, cytosine hydroxymethylation, cytosine formylation, cytosine carboxylation, adenosine methylation, alkylation, or thymine dimerization.

20. The structure of claim 1, wherein:
the first and second actuation molecules of the one or more functional molecules comprise a first protein and a second protein, the first protein being a transmembrane receptor protein capable of binding at least one type of ligand, the second protein capable of binding the first protein when the transmembrane receptor protein is bound by the at least one type of ligand,
one or more copies of the first protein is attached to the first polynucleotide shape,
one or more copies of the second protein is attached to the second polynucleotide shape, and
wherein in the presence of the at least one type of ligand, the second protein is bound to the first protein, thereby shifting the equilibrium conformation of the bistable molecular sensor towards the closed state.

21. The structure of claim 20, wherein the one or more copies of the first protein attached to the first polynucleotide shape are attached by:
a direct linker molecule between the first protein and the first polynucleotide shape,
insertion of the first protein into a protein-lipid nanodisc, the protein-lipid nanodisc capable of being attached to the first polynucleotide shape, or
insertion of the first protein into a DNA-lipid nanodisc formed as part of the first polynucleotide shape.

22. The structure of claim 20, wherein:
the bistable molecular sensor further comprises a G-protein receptor kinase (GRK), the GRK being in solution or attached to the nucleic acid structure,
the first protein comprises a G-protein coupled receptor (GPCR) and the second protein comprises beta-arrestin or an antibody capable of binding phosphorylated GPCR, and
in the presence of the at least one type of receptor ligand to the GPCR, the GPCR is phosphorylated by the GRK and therefore beta-arrestin or the antibody binds the phosphorylated GPCR, thereby shifting the equilibrium conformation of the bistable molecular sensor towards the closed state.

23. The structure of claim 1, wherein:
the first and second actuation molecules of the one or more functional molecules comprise a first molecule and a second molecule, the first molecule comprising a DNA riboswitch or an RNA riboswitch capable of being bound by a riboswitch ligand, the binding of the riboswitch ligand inducing exposure of a nucleotide sequence or aptamer, the second molecule comprising a DNA sequence, an RNA sequence, or a protein capable of binding the exposed nucleotide sequence or aptamer on the DNA riboswitch or RNA riboswitch, one or more copies of the first molecule is attached to the first polynucleotide shape, one or more copies of the second molecule is attached to the second polynucleotide shape, and in the presence of the riboswitch ligand, the second molecule binds to the first molecule, thereby shifting the equilibrium conformation of the bistable molecular sensor towards the closed state.

24. The structure of claim 1, wherein:

the first and second actuation molecules of the one or more functional molecules comprise a capture molecule capable of being modified by a chemical or enzymatic agent to form a modified capture molecule, the capture molecule capable of binding the first polynucleotide shape and the second polynucleotide shape, the modified capture molecule not capable of binding the first polynucleotide shape and the second polynucleotide shape, the capture molecule selected from a protein or a nucleic acid, and one or more copies of the capture molecule is attached the first polynucleotide shape and the second polynucleotide shape, and in the presence of the chemical or enzymatic agent, the capture molecule is modified, thereby shifting the equilibrium conformation of the bistable molecular sensor towards the open state.

25. The structure of claim 1, wherein:

the first and second actuation molecules of the one or more functional molecules comprise a first molecule and a second molecule, at least one of the first molecule and the second molecule capable of being modified by a chemical or enzymatic agent resulting in the first molecule binding to the second molecule, the first molecule and the second molecule being selected from nucleic acids or proteins, one or more copies of the first molecule being attached to the first polynucleotide shape, one or more copies of the second molecule being attached to the second polynucleotide shape, in the presence of the chemical or enzymatic agent, the first molecule and the second molecule are bound together, thereby shifting the equilibrium conformation of the bistable molecular sensor towards the closed state.

26. The structure of claim 1, wherein:

the first and second actuation molecules of the one or more functional molecules comprise a capture molecule and probe molecule, the capture molecule capable of being modified by one of temperature, light, pH, or ionic conditions resulting in a modified capture molecule, the probe molecule capable of binding the modified capture molecule, the capture molecule and the probe molecule each independently being a nucleic acid or a protein, one or more copies of the capture molecule is attached to the first polynucleotide shape, one or more copies of the probe molecule is attached to the second polynucleotide shape, and in the presence of the one of temperature, light, pH, or ionic conditions, the capture molecule is modified and the probe molecule binds the modified capture molecule, thereby shifting the equilibrium conformation of the bistable molecular sensor towards the closed state.

27. The structure of claim 1, wherein the nucleotide barcode is configured to be read out by:

next generation sequencing;

quantitative or real-time PCR;

droplet digital PCR; or deep DNA sequencing.

28. The structure of claim 1, wherein the affinity tag is configured to be used with a separation device comprising:

an affinity column; or streptavidin beads.

29. The structure of claim 1, wherein the nucleic acid structure comprises a polynucleotide platform selected from a scaffolded deoxyribonucleic acid (DNA) origami, scaffolded ribonucleic acid (RNA) origami, scaffolded hybrid DNA:RNA origami, single-stranded DNA tiles, multi-stranded DNA tiles, single-stranded RNA origami, multi-stranded RNA tiles, or hierarchically composed DNA or RNA origami with multiple scaffolds.

* * * * *